United States Patent
Estes et al.

(10) Patent No.: US 9,433,376 B2
(45) Date of Patent: Sep. 6, 2016

(54) SYSTEMS AND METHODS FOR PROCESSING ANALYTE SENSOR DATA

(71) Applicant: DexCom, Inc., San Diego, CA (US)

(72) Inventors: Michael J. Estes, San Diego, CA (US); Stephen J. Vanslyke, Carlsbad, CA (US); Apurv Ullas Kamath, San Diego, CA (US); Thomas A. Peyser, Menlo Park, CA (US); Lucas Bohnett, San Diego, CA (US); Aarthi Mahalingam, San Diego, CA (US); Arturo Garcia, Chula Vista, CA (US); Peter C. Simpson, Encinitas, CA (US); Anna Leigh Rack-Gomer, San Diego, CA (US); Sebastian Bohm, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 615 days.

(21) Appl. No.: 13/796,185

(22) Filed: Mar. 12, 2013

(65) Prior Publication Data
US 2013/0245401 A1    Sep. 19, 2013

Related U.S. Application Data

(60) Provisional application No. 61/612,129, filed on Mar. 16, 2012.

(51) Int. Cl.
| G01N 27/26 | (2006.01) |
| A61B 5/1495 | (2006.01) |
| A61B 5/145 | (2006.01) |
| G01D 3/02 | (2006.01) |
| G06F 19/00 | (2011.01) |

(52) U.S. Cl.
CPC .......... *A61B 5/1495* (2013.01); *A61B 5/14532* (2013.01); *G01D 3/022* (2013.01); *G06F 19/3468* (2013.01); *A61B 2560/0223* (2013.01)

(58) Field of Classification Search
CPC ................. A61B 5/14532; A61B 2560/0223; G01D 3/022
USPC ................ 702/19, 104; 422/400, 403, 68.1; 600/309, 345, 347, 587; 604/66
See application file for complete search history.

(56) References Cited

U.S. PATENT DOCUMENTS

| 4,935,345 A | 6/1990 | Guilbeau et al. |
| 5,112,455 A | 5/1992 | Cozzette et al. |

(Continued)

FOREIGN PATENT DOCUMENTS

| WO | WO 99/07878 | 2/1999 |
| WO | WO 99-07878 | 2/1999 |

(Continued)

OTHER PUBLICATIONS

Noujaim et al. 2007. J. Diabetes Science & Technology 1(5):652-668. Accuracy Requirements for a Hypoglycemia Detector: An Analytical Model to Evaluate the Effects of Bias.

*Primary Examiner* — Carol S Tsai
(74) *Attorney, Agent, or Firm* — Knobbe Martens Olson & Bear, LLP

(57) ABSTRACT

Systems and methods for applying time-dependent algorithmic compensation functions to data output from a continuous analyte sensor. Some embodiments determine a time since sensor implantation and/or whether a newly initialized sensor has been used previously.

43 Claims, 16 Drawing Sheets

(56) References Cited

U.S. PATENT DOCUMENTS

| | | | |
|---|---|---|---|
| 5,352,349 A | 10/1994 | Inamoto et al. | |
| 5,356,217 A | 10/1994 | Sheffield | |
| 5,645,077 A * | 7/1997 | Foxlin | A61B 5/1114 600/587 |
| 5,980,728 A | 11/1999 | Farber et al. | |
| 6,486,661 B2 * | 11/2002 | Chia | G01C 25/005 324/105 |
| 6,558,351 B1 | 5/2003 | Steil et al. | |
| 6,560,471 B1 | 5/2003 | Heller et al. | |
| 6,850,859 B1 * | 2/2005 | Schuh | G01D 18/008 324/105 |
| 6,893,396 B2 * | 5/2005 | Schulze | A61B 5/0022 128/903 |
| 6,990,422 B2 | 1/2006 | Laletin et al. | |
| 7,029,444 B2 | 4/2006 | Shin et al. | |
| 7,253,680 B2 | 8/2007 | Laletin | |
| 7,299,082 B2 | 11/2007 | Feldman et al. | |
| 7,338,639 B2 | 3/2008 | Burke et al. | |
| 7,390,667 B2 | 6/2008 | Burke et al. | |
| 7,407,811 B2 | 8/2008 | Burke et al. | |
| 7,488,601 B2 | 2/2009 | Burke et al. | |
| 7,494,816 B2 | 2/2009 | Burke et al. | |
| 7,653,425 B2 | 1/2010 | Hayter et al. | |
| 7,774,038 B2 | 8/2010 | Wang et al. | |
| 7,776,559 B2 | 8/2010 | Childers et al. | |
| 7,778,679 B2 | 8/2010 | Schulman et al. | |
| 7,866,025 B2 * | 1/2011 | James | B64C 27/56 29/458 |
| 7,920,906 B2 | 4/2011 | Goode et al. | |
| 7,938,797 B2 * | 5/2011 | Estes | A61M 5/14244 604/503 |
| 7,985,330 B2 | 7/2011 | Wang et al. | |
| 8,000,763 B2 | 8/2011 | Mazza et al. | |
| 8,112,240 B2 | 2/2012 | Fennell | |
| 8,114,268 B2 | 2/2012 | Wang et al. | |
| 8,160,834 B2 | 4/2012 | Liang et al. | |
| 8,224,415 B2 * | 7/2012 | Budiman | A61B 5/14532 600/347 |
| 8,249,683 B2 | 8/2012 | Wang et al. | |
| 8,348,923 B2 | 1/2013 | Kanderian et al. | |
| 8,372,351 B2 * | 2/2013 | Ow-Wing | A61B 5/0002 422/400 |
| 8,560,037 B2 * | 10/2013 | Goode, Jr. | A61B 5/0031 600/345 |
| 8,942,778 B2 * | 1/2015 | Ocvirk | A61B 5/14865 600/345 |
| 2002/0161288 A1 | 10/2002 | Shin et al. | |
| 2003/0175987 A1 | 9/2003 | Verdonk et al. | |
| 2004/0108226 A1 | 6/2004 | Polychronakos et al. | |
| 2004/0147819 A1 | 7/2004 | Caduff et al. | |
| 2004/0158137 A1 | 8/2004 | Eppstein et al. | |
| 2006/0142651 A1 | 6/2006 | Brister et al. | |
| 2006/0189863 A1 | 8/2006 | Peyser et al. | |
| 2007/0016381 A1 | 1/2007 | Kamath et al. | |
| 2007/0169533 A1 | 7/2007 | Shah et al. | |
| 2007/0170073 A1 | 7/2007 | Wang et al. | |
| 2007/0173712 A1 | 7/2007 | Shah et al. | |
| 2007/0173741 A1 | 7/2007 | Deshmukh et al. | |
| 2007/0299617 A1 * | 12/2007 | Willis | A61B 5/14532 702/19 |
| 2008/0000779 A1 | 1/2008 | Wang et al. | |
| 2008/0039702 A1 | 2/2008 | Hayter et al. | |
| 2008/0081000 A1 | 4/2008 | MacLeod et al. | |
| 2008/0156661 A1 | 7/2008 | Cooper et al. | |
| 2008/0161664 A1 | 7/2008 | Mastrototaro et al. | |
| 2008/0269714 A1 | 10/2008 | Mastrototaro et al. | |
| 2008/0312844 A1 | 12/2008 | Hayter | |
| 2009/0143659 A1 | 6/2009 | Li et al. | |
| 2009/0240193 A1 * | 9/2009 | Mensinger | A61B 5/7445 604/66 |
| 2010/0025238 A1 | 2/2010 | Gottlieb et al. | |
| 2010/0049021 A1 | 2/2010 | Jina et al. | |
| 2010/0064764 A1 | 3/2010 | Hayter et al. | |
| 2010/0169035 A1 | 7/2010 | Liang et al. | |
| 2010/0179402 A1 * | 7/2010 | Goode, Jr. | A61B 5/0031 600/309 |
| 2010/0191085 A1 | 7/2010 | Budiman | |
| 2010/0230285 A1 * | 9/2010 | Hoss | A61B 5/14532 204/415 |
| 2010/0234710 A1 | 9/2010 | Budiman et al. | |
| 2010/0274107 A1 | 10/2010 | Boock et al. | |
| 2010/0299597 A1 * | 11/2010 | Shin | G06F 3/0482 715/702 |
| 2010/0305421 A1 * | 12/2010 | Ow-Wing | A61B 5/0002 600/365 |
| 2010/0331650 A1 * | 12/2010 | Batman | A61B 5/14532 600/365 |
| 2011/0004085 A1 * | 1/2011 | Mensinger | A61B 5/0031 600/365 |
| 2011/0029269 A1 | 2/2011 | Hayter et al. | |
| 2011/0040163 A1 | 2/2011 | Telson et al. | |
| 2011/0174638 A1 | 7/2011 | Katsuki | |
| 2011/0230741 A1 | 9/2011 | Liang et al. | |
| 2011/0320130 A1 * | 12/2011 | Valdes | G06F 19/3418 702/19 |
| 2013/0060105 A1 | 3/2013 | Shah et al. | |
| 2013/0216434 A1 * | 8/2013 | Ow-Wing | A61B 5/0002 422/68.1 |
| 2013/0225959 A1 * | 8/2013 | Bugler | A61B 5/1495 600/365 |
| 2014/0046155 A1 | 2/2014 | Hayter et al. | |
| 2014/0046156 A1 | 2/2014 | Hayter et al. | |
| 2014/0127821 A1 * | 5/2014 | Petyt | G01N 27/3272 436/95 |
| 2015/0005601 A1 * | 1/2015 | Hoss | A61B 5/14532 600/345 |

FOREIGN PATENT DOCUMENTS

| | | |
|---|---|---|
| WO | WO 99/08485 | 2/1999 |
| WO | WO 99-08485 | 2/1999 |
| WO | WO 00/74753 | 12/2000 |
| WO | WO 00-74753 | 12/2000 |
| WO | WO 2006-008505 | 1/2006 |
| WO | WO 2006/008505 | 1/2006 |
| WO | WO 2010-078263 | 7/2010 |
| WO | WO 2010/078263 | 7/2010 |

* cited by examiner

SYSTEMS AND METHODS FOR PROCESSING ANALYTE SENSOR DATA

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 61/612,129, filed Mar. 16, 2012, the disclosure of which is hereby expressly incorporated by reference in its entirety and is hereby expressly made a portion of this application.

FIELD OF THE INVENTION

The present embodiments relate to systems and methods for processing analyte sensor data from a continuous analyte sensor, including adaptive algorithms.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements can be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

After the sensor is implanted, it is calibrated, after which it provides substantially continuous sensor data to the sensor electronics. The sensor electronics convert the sensor data so that estimated analyte values can be continuously provided to the user. As used herein, the terms "substantially continuous," "continuously," etc., may refer to a data stream of individual measurements taken at time-spaced intervals, which may range from fractions of a second up to, for example, 1, 2, or 5 minutes or more. As the sensor electronics continue to receive sensor data, the sensor may be occasionally recalibrated to account for possible changes in sensor sensitivity and/or baseline (drift). Sensor sensitivity may refer to an amount of electrical current produced in the sensor by a predetermined amount of the measured analyte. Sensor baseline may refer to a signal output by the sensor when no analyte is detected. Over time, sensitivity and baseline change due to a variety of factors. Example factors include cellular attack or migration of cells to the sensor, which can affect the ability of the analyte to reach the sensor. Preferably, drift is taken into consideration when applying a conversion function to the raw data, so that accurate readings can be provided to the user.

SUMMARY OF THE INVENTION

The various embodiments of the present systems and methods for processing analyte sensor data have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present embodiments includes the realization that, with some sensors, typically the greatest rate of drift occurs during the first day to three days after implantation of a new sensor, after which the rate of change of drift typically levels off. Thus, the need to recalibrate the sensor is greatest during the first day to three days after implantation. However, lack of host compliance can lead to difficulty in properly recalibrating the sensor. For example, current government regulations require that today's sensors be replaced at mandated intervals. However, the more sensors a host uses, the more sensors he or she must purchase. Thus, there is an economic incentive for hosts to reuse old sensors rather than always implanting a new sensor at the end of each life cycle. If it is assumed that each sensor is new when it is initialized, improper assumptions about calibration/recalibration may be applied to the sensor, and the host may receive an artificially inflated or deflated reading of his or her blood glucose, with possible attendant side effects. It would thus be beneficial if it could be determined whether a sensor is new or has been reused, so that appropriate drift compensation, for example, could be applied to the signal output by the sensor.

In a first aspect, a method for processing sensor data output by a continuous analyte sensor implanted within a body is provided, the method comprising: measuring a change in sensitivity or baseline of the sensor over a time interval; determining a drift compensation function to be applied to a plurality of time-spaced data points output by the sensor; and applying the drift compensation function continuously to the data points.

In an embodiment of the first aspect, measuring the change in sensitivity or baseline of the sensor comprises comparing a first measured sensitivity or baseline of the sensor to a second measured sensitivity or baseline of the sensor, wherein the first and second measured sensitivities or baselines of the sensor are taken at a beginning and an end, respectively, of the time interval.

The drift compensation function may be determined based on rate of change in sensitivity or baseline of the sensor as determined from the measuring step.

In an embodiment of the first aspect, which is generally applicable, particularly with any other embodiment of the first aspect, measuring the change in sensitivity or baseline of the sensor comprises comparing a measured sensitivity or baseline of the sensor to a predetermined sensitivity or baseline of the sensor. The predetermined sensitivity or baseline of the sensor may be based on an earlier measurement thereof and may be retrieved from memory.

The change in sensitivity or baseline may be obtained from reference analyte data, which is not taken from the sensor analyte measurements. That is, the change in sensitivity or baseline is preferably taken from a separate test from the analyte measurements being made by the analyte sensor.

In an embodiment of the first aspect, a value of the predetermined sensitivity or baseline of the sensor is assigned according to known characteristics of the body in which the sensor is implanted.

In an embodiment of the first aspect, the characteristics include at least one of age, body type, gender, diabetes type, diabetes duration, concomitant diseases and/or sensor location.

In an embodiment of the first aspect, the predetermined sensitivity or baseline of the sensor is based on a measured impedance of the sensor.

In an embodiment of the first aspect, the impedance of the sensor is measured in vitro.

In an embodiment of the first aspect, the impedance of the sensor is measured in vivo.

In an embodiment of the first aspect, determining a drift compensation function to be applied is based, at least in part, on the predetermined sensitivity or baseline. The drift compensation function may be based on the measured change in sensitivity or baseline over time.

In an embodiment of the first aspect, a value of the predetermined sensitivity or baseline is encoded on electronics associated with the sensor.

An embodiment of the first aspect, which is generally applicable, particularly with any other embodiment of the first aspect, further comprises comparing the measured change in sensitivity or baseline of the sensor to a priori knowledge regarding the change in sensitivity or baseline of the sensor over the time interval.

An embodiment of the first aspect, which is generally applicable, particularly with any other embodiment of the first aspect, further comprises based on the measured change in sensitivity or baseline of the sensor, determining whether the sensor has been previously used.

In an embodiment of the first aspect, which is generally applicable, particularly with any other embodiment of the first aspect, measuring the change in sensitivity of the sensor over the time interval comprises calculating a drift rate of the sensor over the time interval. The drift compensation function may be determined based on the drift rate.

In an embodiment of the first aspect, which is generally applicable, particularly with any other embodiment of the first aspect, measuring the drift rate of the sensor comprises comparing measured analyte values to substantially time-corresponding reference analyte values over the time interval.

An embodiment of the first aspect, which is generally applicable, particularly with any other embodiment of the first aspect, further comprises calculating an expected drift rate of the sensor based on a weighted average of a current measured drift rate and at least one previously measured drift rate.

In an embodiment of the first aspect, which is generally applicable, particularly with any other embodiment of the first aspect, measuring the change in sensitivity or baseline of the sensor occurs only after the sensor has been implanted within the body for at least a minimum duration.

An embodiment of the first aspect, which is generally applicable, particularly with any other embodiment of the first aspect, further comprises measuring a temperature of the body.

An embodiment of the first aspect further comprises using the measured temperature to adjust the measured change in sensitivity or baseline of the sensor.

An embodiment of the first aspect further comprises using the measured temperature as an input when determining the drift compensation function to be applied.

In an embodiment of the first aspect, which is generally applicable, particularly with any other embodiment of the first aspect, measuring the change in sensitivity or baseline of the sensor comprises measuring a change in impedance of the sensor.

An embodiment of the first aspect, which is generally applicable, particularly with any other embodiment of the first aspect, further comprises prompting a user for a reference analyte value when the measured change in sensitivity or baseline of the sensor exceeds a criterion.

An embodiment of the first aspect, which is generally applicable, particularly with any other embodiment of the first aspect, further comprises storing the change in sensitivity or baseline of the sensor for later use.

In an embodiment of the first aspect, which is generally applicable, particularly with any other embodiment of the first aspect, the applied drift compensation function is a stepwise function. A scaling factor applied to the sensor data for drift compensation may be calculated at each step. The calculation of the scaling factor may be based on data or parameters from calibration operations. In particular, the calculation may be based on a drift rate in parameters obtained from time separated calibration operations, the parameters for defining a relationship between raw sensor data and reference analyte data.

In an embodiment of the first aspect, which is generally applicable, particularly with any other embodiment of the first aspect, the applied drift compensation function is a mathematical inverse of a mathematical equation that describes the change in sensitivity or baseline of the sensor over the time interval.

In an embodiment of the first aspect, which is generally applicable, particularly with any other embodiment of the first aspect, a priori knowledge of sensor sensitivity and/or baseline drift is used to model and apply drift compensation within a Kalman filter framework.

An embodiment of the first aspect, which is generally applicable, particularly with any other embodiment of the first aspect, further comprises applying boundaries to the drift compensation function.

In an embodiment of the first aspect, the boundaries are based on a priori knowledge.

In an embodiment of the first aspect, which is generally applicable, particularly with any other embodiment of the first aspect, measuring the change in sensitivity or baseline of the sensor comprises taking two distinct measurements according to two distinct techniques.

An embodiment of the first aspect, which is generally applicable, particularly with any other embodiment of the first aspect, further comprises measuring an absolute sensitivity or baseline of the sensor at a time t, and wherein determining the drift compensation function to be applied to the plurality of time-spaced data points output by the sensor is based on the measured absolute sensitivity or baseline.

An embodiment of the first aspect, which is generally applicable, particularly with any other embodiment of the first aspect, further comprises ceasing applying the drift compensation function continuously to the data points when the measured change in sensitivity or baseline of the sensor is below a threshold value.

An embodiment of the first aspect, which is generally applicable, particularly with any other embodiment of the first aspect, further comprises ceasing applying the drift compensation function continuously to the data points after a predetermined amount of time has elapsed.

In an embodiment of the first aspect, the step of measuring a change in sensitivity or baseline of the sensor occurs over a first time interval, the step of determining a drift compensation function is based on the measured change in sensitivity or baseline of the sensor over the first time interval, and the step of applying the drift compensation function is to continuously adjust the sensor data output to compensate for changes in sensitivity or baseline of the sensor over a second time interval.

In a second aspect, a system for processing data is provided, the system comprising: a continuous analyte sensor configured to be implanted within a body; and sensor electronics configured to receive and process sensor data output by the sensor, the sensor electronics including a processor configured to measure a change in sensitivity or baseline of the sensor over an interval of time; determine a drift compensation function to be applied to a plurality of time-spaced data points output by the sensor over a next interval of time; and apply the drift compensation function continuously to the data points over the next interval of time.

In an embodiment of the second aspect, measuring the change in sensitivity or baseline of the sensor comprises comparing a first measured sensitivity or baseline of the sensor to a second measured sensitivity or baseline of the sensor, wherein the first and second measured sensitivities or baselines of the sensor are taken at a beginning and an end, respectively, of the time interval.

In an embodiment of the second aspect, the processor is further configured to compare a measured sensitivity or baseline of the sensor to a predetermined sensitivity or baseline of the sensor.

In an embodiment of the second aspect, a value of the predetermined sensitivity or baseline of the sensor is assigned according to known characteristics of the body in which the sensor is implanted.

In an embodiment of the second aspect, the characteristics include at least one of age, body type, gender, diabetes type, diabetes duration, concomitant diseases and/or sensor location.

In an embodiment of the second aspect, the predetermined sensitivity or baseline of the sensor is based on a measured impedance of the sensor.

In an embodiment of the second aspect, the impedance of the sensor is measured in vitro.

In an embodiment of the second aspect, the impedance of the sensor is measured in vivo.

In an embodiment of the second aspect, determining a drift compensation function to be applied is based, at least in part, on the predetermined sensitivity or baseline.

In an embodiment of the second aspect, a value of the predetermined sensitivity or baseline is encoded on the sensor electronics.

In an embodiment of the second aspect, the processor is further configured to compare the measured change in sensitivity or baseline of the sensor to a priori knowledge regarding the change in sensitivity or baseline of the sensor over the time interval.

In an embodiment of the second aspect, measuring the change in sensitivity of the sensor over the time interval comprises calculating a drift rate of the sensor over the time interval.

In an embodiment of the second aspect, measuring the drift rate of the sensor comprises comparing measured analyte values to substantially time-corresponding reference analyte values over the time interval.

In an embodiment of the second aspect, the processor is further configured to calculate an expected drift rate of the sensor based on a weighted average of a current measured drift rate and at least one previously measured drift rate.

In an embodiment of the second aspect, measuring the change in sensitivity or baseline of the sensor occurs only after the sensor has been implanted within the body for at least a minimum duration.

An embodiment of the second aspect further comprises a temperature sensor configured to measure a temperature of the body.

In an embodiment of the second aspect, the processor is further configured to use the measured temperature to adjust the measured change in sensitivity or baseline of the sensor.

In an embodiment of the second aspect, the processor is further configured to use the measured temperature as an input when determining the drift compensation function to be applied.

In an embodiment of the second aspect, measuring the change in sensitivity or baseline of the sensor comprises measuring a change in impedance of the sensor.

In an embodiment of the second aspect, the processor is further configured to prompt a user for a reference analyte value when the measured change in sensitivity or baseline of the sensor exceeds a criteria.

In an embodiment of the second aspect, the processor is further configured to store the change in sensitivity or baseline of the sensor for later use.

In an embodiment of the second aspect, the applied drift compensation function is a stepwise function.

In an embodiment of the second aspect, the applied drift compensation function is a mathematical inverse of a mathematical equation that describes the change in sensitivity or baseline of the sensor over the time interval.

In an embodiment of the second aspect, a priori knowledge of sensor sensitivity and/or baseline drift is used to model and apply drift compensation within a Kalman filter framework.

In an embodiment of the second aspect, the processor is further configured to apply boundaries to the drift compensation function.

In an embodiment of the second aspect, the boundaries are based on a priori knowledge.

In an embodiment of the second aspect, measuring the change in sensitivity or baseline of the sensor comprises taking two distinct measurements according to two distinct techniques.

In an embodiment of the second aspect, the processor is further configured to measure an absolute sensitivity or baseline of the sensor at a time t, and wherein determining the drift compensation function to be applied to the plurality of time-spaced data points output by the sensor is based on the measured absolute sensitivity or baseline.

In an embodiment of the second aspect, the processor is further configured to cease applying the drift compensation function continuously to the data points when the measured change in sensitivity or baseline of the sensor is below a threshold value.

In an embodiment of the second aspect, the processor is further configured to cease applying the drift compensation function continuously to the data points after a predetermined amount of time has elapsed.

In an embodiment of the second aspect, the processor is configured to determine a drift compensation function based on the measured change in sensitivity or baseline of the sensor over the interval of time, and to apply the drift compensation function continuously to the data points over the next interval of time to continuously adjust the sensor data output to compensate for changes in sensitivity or baseline of the sensor over a second time interval.

In a third aspect, a method for processing sensor data of a continuous analyte sensor implanted within a body is provided, the method comprising: initializing the sensor; applying a first (set of) time-dependent algorithmic function(s) to data associated with the sensor during a first interval based on a first elapsed time since the sensor was implanted; and applying a second (set of) time-dependent algorithmic function(s) to the data associated with the sensor during a second interval after the first interval based on a second elapsed time since the sensor was implanted.

In an embodiment of the third aspect, which is generally applicable, particularly with any other embodiment of the third aspect, initializing the sensor comprises engaging electronics associated with the sensor with a housing.

In an embodiment of the third aspect, which is generally applicable, particularly with any other embodiment of the third aspect, engagement of the electronics with the receiving unit is detected and initialization commences automatically upon detection of the engagement.

In an embodiment of the third aspect, which is generally applicable, particularly with any other embodiment of the third aspect, initializing the sensor comprises prompting a user via a user interface associated with the sensor.

In an embodiment of the third aspect, which is generally applicable, particularly with any other embodiment of the third aspect, the user commences the initialization by entering a command via a menu on the user interface.

An embodiment of the third aspect, which is generally applicable, particularly with any other embodiment of the third aspect, further comprises determining whether the sensor has been previously used.

In an embodiment of the third aspect, determining whether the sensor has been previously used comprises: determining a time, delta T, since the prior sensor session ended and the current sensor session was initialized; if T is less than a threshold value, determining that the sensor has not been previously used; and if T is greater than the threshold value, determining that the sensor has been previously used.

In an embodiment of the third aspect, determining whether the sensor has been previously used comprises prompting a user for input.

In an embodiment of the third aspect, the input is a unique number associated with the sensor.

In an embodiment of the third aspect, determining whether the sensor has been previously used comprises reading a radio frequency identifier associated with the sensor.

In an embodiment of the third aspect, determining whether the sensor has been previously used comprises comparing a conversion function of the sensor with a conversion function of a previously removed sensor.

In an embodiment of the third aspect, determining whether the sensor has been previously used comprises: measuring a change in impedance of the sensor over a time, T; if the change in the impedance is less than a threshold value, determining that the sensor has been previously used; and if the change in the impedance is greater than the threshold value, determining that the sensor has not been previously used.

In an embodiment of the third aspect, determining whether the sensor has been previously used comprises reading a raw signal of the sensor.

In an embodiment of the third aspect, determining whether the sensor has been previously used comprises comparing a sensitivity and/or baseline of the sensor with a sensitivity and/or baseline of a previously removed sensor.

In an embodiment of the third aspect, determining whether the sensor has been previously used comprises comparing a trend in a signal from the sensor with a trend in a signal from a previously removed sensor.

In an embodiment of the third aspect, determining whether the sensor has been previously used comprises performing two or more independent tests and then determining a probability that the sensor has been previously used based upon results of the tests.

In an embodiment of the third aspect, a result of a first one of the two or more independent tests that is likely to be more reliable is weighted more heavily than a result of a second one of the two or more independent tests that is likely to be less reliable.

In an embodiment of the third aspect, the above embodiments for determining whether the sensor has been previously used may be combined in any way. That is, any two, three or more of the embodiments for determining whether the sensor has been used may be combined.

In an embodiment of the third aspect, which is generally applicable, particularly with any other embodiment of the third aspect, applying the first set of time-dependent algorithmic functions comprises applying drift compensation to the data associated with the sensor.

In an embodiment of the third aspect, which is generally applicable, particularly with any other embodiment of the third aspect, the first and second set of time-dependent algorithmic functions comprise first and second boundaries of acceptability.

In an embodiment of the third aspect, the first boundary comprises a first sensitivity value and the second boundary comprises a second sensitivity value.

In an embodiment of the third aspect, the first boundary comprises a first baseline value and the second boundary comprises a second baseline value.

In an embodiment of the third aspect, the first boundary delineates a first acceptable deviation of one or more match data pairs and the second boundary delineates a second acceptable deviation of one or more matched data pairs.

In an embodiment of the third aspect, the first boundary comprises a first drift rate of the sensitivity over a time period and the second boundary comprises a second drift rate of the sensitivity over time.

In an embodiment of the third aspect, the first boundary comprises a first drift rate of the baseline over a time period and the second boundary comprises second drift rate of the baseline over time.

In an embodiment of the third aspect, the first boundary delineates acceptable slopes and baselines of a conversion function and the second boundary delineates acceptable slopes and baselines of the conversion function.

In an embodiment of the third aspect, the second boundary is higher than the first boundary In an embodiment of the third aspect, the second boundary is lower than the first boundary In an embodiment of the third aspect, the second boundary comprises a range that is more narrow than the first boundary In an embodiment of the third aspect, the second boundary comprises a range that is wider than the first boundary.

In an embodiment of the third aspect, which is generally applicable, particularly with any other embodiment of the third aspect, the first and second set of time-dependent algorithmic functions comprise first and second parameters associated with the conversion function.

In an embodiment of the third aspect, the first and second parameters associated with the conversion function define a number of matched data pairs or a window of time over which matched data pairs may be included in a calibration set, wherein the conversion function is based on the calibration set.

In an embodiment of the third aspect, the conversion function is based on predetermined baseline information, and wherein the first and second parameters comprise first and second baseline information.

In an embodiment of the third aspect, the wherein the first and second set of time-dependent algorithmic functions comprise first and second drift compensation functions.

In an embodiment, the method comprises determining the second drift compensation function based on more recent sensor drift data than that used to determine the first drift compensation function. The first drift compensation function may be determined based on data or parameters used in first and second time separated calibration operations for determining respective conversion functions for converting raw sensor data to analyte data. The second drift compensation function may be determined based on data or parameters used a third calibration operation subsequent to the second calibration operation and used in at least one of the first and second calibration operations. In particular, the first and second drift compensation functions are determined based on sensor drift rate data obtained from preceding calibration operations. The second drift compensation function is determined based on sensor drift rate data from more recent calibration operations than those used for determining the first drift compensation function.

In an embodiment of the third aspect, the first and second drift compensation functions differ in the amount of drift compensation that they apply.

In a fourth aspect, a system for processing sensor data of a continuous analyte sensor implanted within a body is provided, the system comprising: a continuous analyte sensor configured to be implanted within a body; and sensor electronics configured to receive and process sensor data output by the sensor, the sensor electronics including a processor configured to initialize the sensor; apply a first (set of) time-dependent algorithmic function(s) to data associated with the sensor during a first interval based on a first elapsed time since the sensor was implanted; and apply a second (set of) time-dependent algorithmic function(s) to the data associated with the sensor during a second interval after the first interval based on a second elapsed time since the sensor was implanted.

In an embodiment of the fourth aspect, initialization of the sensor commences automatically when the sensor electronics engages a housing.

In an embodiment of the fourth aspect, initialization of the sensor commences after a user enters a command on a user interface associated with the sensor.

In an embodiment of the fourth aspect, the processor is further configured to determine whether the sensor has been previously used.

In an embodiment of the fourth aspect, determining whether the sensor has been previously used comprises: determining a time, delta T, since the prior sensor session ended and the current sensor session was initialized; if T is less than a threshold value, determining that the sensor has not been previously used; and if T is greater than the threshold value, determining that the sensor has been previously used.

In an embodiment of the fourth aspect, determining whether the sensor has been previously used comprises prompting a user for input.

In an embodiment of the fourth aspect, the input is a unique number associated with the sensor.

In an embodiment of the fourth aspect, determining whether the sensor has been previously used comprises reading a radio frequency identifier associated with the sensor.

In an embodiment of the fourth aspect, determining whether the sensor has been previously used comprises comparing a conversion function of the sensor with a conversion function of a previously removed sensor.

In an embodiment of the fourth aspect, determining whether the sensor has been previously used comprises: measuring a change in impedance of the sensor over a time, T; if the change in the impedance is less than a threshold value, determining that the sensor has been previously used; and if the change in the impedance is greater than the threshold value, determining that the sensor has not been previously used.

In an embodiment of the fourth aspect, determining whether the sensor has been previously used comprises reading a raw signal of the sensor.

In an embodiment of the fourth aspect, determining whether the sensor has been previously used comprises comparing a sensitivity and/or baseline of the sensor with a sensitivity and/or baseline of a previously removed sensor.

In an embodiment of the fourth aspect, determining whether the sensor has been previously used comprises comparing a trend in a signal from the sensor with a trend in a signal from a previously removed sensor.

In an embodiment of the fourth aspect, determining whether the sensor has been previously used comprises performing two or more independent tests and then determining a probability that the sensor has been previously used based upon results of the tests.

In an embodiment of the fourth aspect, a result of a first one of the two or more independent tests that is likely to be more reliable is weighted more heavily than a result of a second one of the two or more independent tests that is likely to be less reliable.

In an embodiment of the fourth aspect, applying the first set of time-dependent algorithmic functions comprises applying drift compensation to the data associated with the sensor.

In an embodiment of the fourth aspect, the first and second set of time-dependent algorithmic functions comprise first and second boundaries of acceptability.

In an embodiment of the fourth aspect, the first boundary comprises a first sensitivity value and the second boundary comprises a second sensitivity value.

In an embodiment of the fourth aspect, the first boundary comprises a first baseline value and the second boundary comprises a second baseline value.

In an embodiment of the fourth aspect, the first boundary delineates a first acceptable deviation of one or more match data pairs and the second boundary delineates a second acceptable deviation of one or more matched data pairs.

In an embodiment of the fourth aspect, the first boundary comprises a first drift rate of the sensitivity over a time period and the second boundary comprises second drift rate of the sensitivity over time.

In an embodiment of the fourth aspect, the first boundary comprises a first drift rate of the baseline over a time period and the second boundary comprises second drift rate of the baseline over time.

In an embodiment of the fourth aspect, the first boundary delineates acceptable slopes and baselines of a conversion function and the second boundary delineates acceptable slopes and baselines of the conversion function.

In an embodiment of the fourth aspect, the second boundary is higher than the first boundary In an embodiment of the fourth aspect, the second boundary is lower than the first boundary In an embodiment of the fourth aspect, the second boundary comprises a range that is more narrow than the first boundary In an embodiment of the fourth aspect, the second boundary comprises a range that is wider than the first boundary.

In an embodiment of the fourth aspect, the first and second set of time-dependent algorithmic functions comprise first and second parameters associated with the conversion function.

In an embodiment of the fourth aspect, the first and second parameters associated with the conversion function define a number of matched data pairs or a window of time over which matched data pairs may be included in a calibration set, wherein the conversion function is based on the calibration set.

In an embodiment of the fourth aspect, the conversion function is based on predetermined baseline information, and wherein the first and second parameters comprises first and second baseline information.

In an embodiment of the fourth aspect, the first and second set of time-dependent algorithmic functions comprise first and second drift compensation functions.

In an embodiment of the fourth aspect, the first and second drift compensation functions differ in the amount of drift compensation that they apply.

The above first and second aspects and the associated embodiments are combinable with the above third and fourth aspects and associated embodiments. In one form, the step of measuring the change in sensitivity of the first and second aspects and associated embodiments may be used to determine the first and/or second time dependent algorithms of the third and fourth aspects and associated embodiments. Additionally or alternatively, the step of determining a drift compensation function of the first and second aspects and associated embodiments can be used to determine the first and/or second time dependent algorithms of the third and fourth aspects. Additionally or alternatively, the initializing step of the third and fourth aspects and associated embodiments is applicable to the third and fourth aspects and associated embodiments.

In a fifth aspect, there is provided a method comprising converting raw sensor data from an analyte sensor implanted within a body to analyte sensor data using a conversion function; and applying a drift compensation function to the raw sensor data or the analyte sensor data to compensate for sensor drift in a responsiveness of the analyte sensor to an analyte being sensed.

The feature of converting raw sensor data from an analyte sensor to analyte data using a conversion function is applicable to all aspects and embodiments identified herein. Further, the feature concerning measuring the change in sensitivity in the above first and second aspects (and associated embodiments) may be made optional. Conversely, the measuring feature of the first and second aspects (and the associated embodiments) is applicable to the other aspects including the fifth aspect. The initializing step of the third and fourths aspect (and the associated embodiments) is applicable to the fifth aspect. The differing features of the above first to fourth aspects and the associated embodiments are combinable with the fifth aspect.

In a generally applicable embodiment (i.e. independently combinable with any of the aspects or embodiments identified herein), the drift compensation function is applied to the sensor data to vary the sensor data over a time interval over which the conversion function does not vary.

In a generally applicable embodiment, the drift compensation function is applied to vary sensor data over time increments between successive calibrations of the conversion function. Thus, the sensor data is varied at small time steps during a relatively long time interval between calibration events when a constant conversion function is used.

In a generally applicable embodiment, the conversion function is set based on a relationship between reference analyte data and raw sensor data. Analyte sensor drift causes this relationship to vary over time, which variance is compensated for by the drift compensation function.

In a generally applicable embodiment, the drift compensation function is derived from a change in a relationship between raw sensor data and reference analyte data over a preceding time interval. The change in a relationship may be in the form of a rate of change. The reference analyte data is determined otherwise than by way of the conversion function. For example, a separate test for the analyte could be performed (e.g. blood test).

In a generally applicable embodiment, time separated conversion functions are determined in respective calibration operations, the conversion functions respectively defining a relationship between raw sensor data and reference analyte data, wherein the drift compensation function is derived from a change in (e.g. one or more parameters of) conversion functions over time.

In a generally applicable embodiment, the drift compensation function is determined based on data or parameters from at least two calibration events for determining respective conversion functions.

In a generally applicable embodiment, the drift compensation function is determined at a first point in time and redetermined at a later point in time based on more recent data. In particular, the drift compensation function is determined at each of time spaced calibration events and the drift compensation function is determined based on data or parameters at least from the more recent calibration process and preferably also from at least the directly preceding calibration process. In a generally applicable embodiment, the drift compensation function defines a scaling factor or function applied to the sensor data such that the magnitude of the sensor data varies with time.

In a generally applicable embodiment, a frequency of conversion function calibrations is varied depending upon a drift rate of the sensor as derivable from the drift compensation function. This is also an independently applicable aspect in that a method could be provided in which a conversion function is used to convert raw sensor data from an analyte sensor implanted within a body to analyte data, wherein the conversion function is calibrated at time intervals, wherein a frequency of calibrations is set depending upon a determined drift rate of the analyte sensor with regard to its responsiveness to the analyte being sensed. A more recent calibration is based on more recent data concerning a relationship between raw sensor data and reference analyte data.

In a generally applicable embodiment, a frequency of conversion function calibration requests is varied depending upon a drift rate of the sensor as derivable from the drift compensation function. This is also an independently applicable aspect in that a method could be provided in which a conversion function is used to convert raw sensor data from an analyte sensor implanted within a body to analyte data, wherein the conversion function is calibrated at time intervals, wherein a frequency of calibration requests is set depending upon a determined drift rate of the analyte sensor with regard to its responsiveness to the analyte being sensed. A more recent calibration is based on more recent data concerning a relationship between raw sensor data and reference analyte data. A calibration request may be provided in the form or a prompt for reference analyte data. The request may be a request to a user.

In a generally applicable embodiment, a frequency of conversion function calibrations or requests therefor increases as a drift rate increases.

In a generally applicable embodiment, drift compensation ceases to be applied after a set amount of time or after a determination that sensor drift rate is sufficiently low.

In further aspects and embodiments, the above method features are formulated in terms of a system having the analyte sensor and control means configured to carry out the method features.

BRIEF DESCRIPTION OF THE DRAWINGS

The various embodiments of the present systems and methods for processing analyte sensor data now will be discussed in detail with an emphasis on highlighting the advantageous features. These embodiments depict the novel and non-obvious systems and methods shown in the accompanying drawings, which are for illustrative purposes only. These drawings include the following figures, in which like numerals indicate like parts.

DETAILED DESCRIPTION

Figure 1:
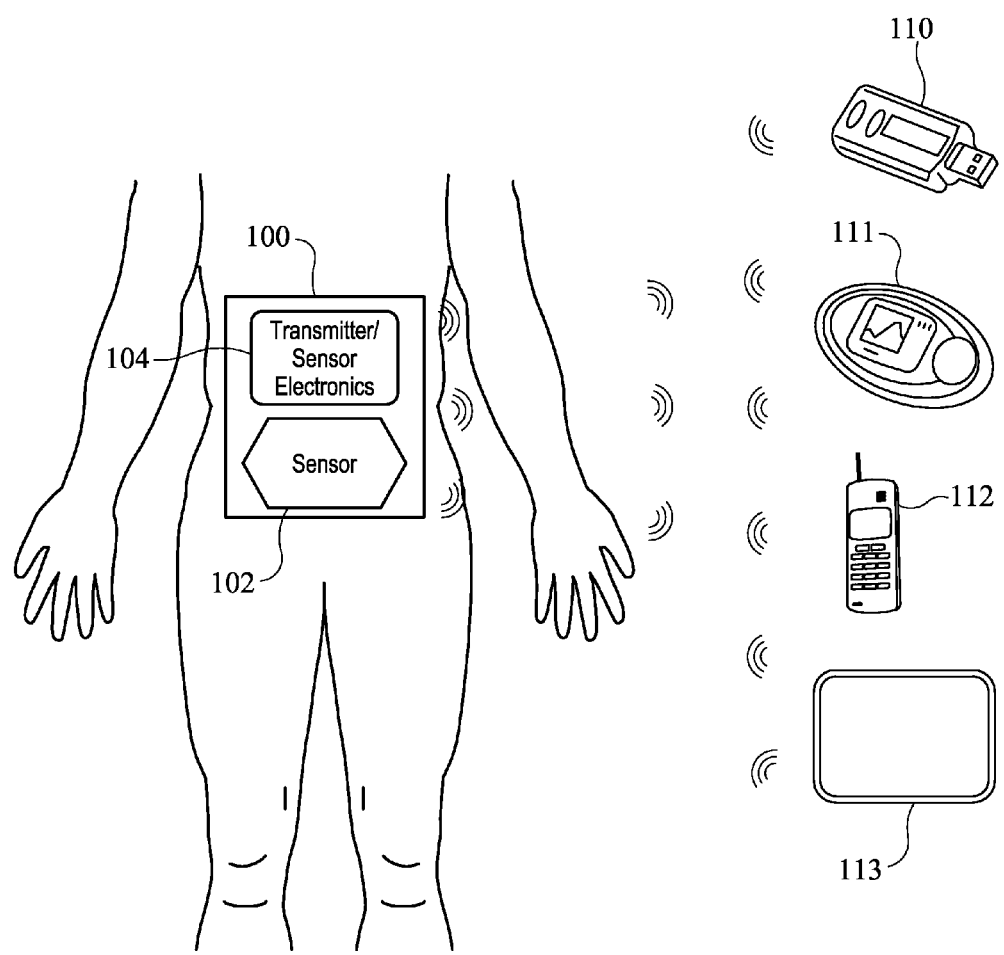
FIG. 1 is a schematic view of a continuous analyte sensor system attached to a host and communicating with a plurality of example devices.

The following detailed description describes the present embodiments with reference to the drawings. In the drawings, reference numbers label elements of the present embodiments. These reference numbers are reproduced below in connection with the discussion of the corresponding drawing features.

Sensor System and Applicator

FIG. 1 is a schematic view of a continuous analyte sensor system 100 attached to a host and communicating with a number of example devices 110-113. A transcutaneous analyte sensor system comprising an on-skin sensor assembly 100 is fastened to the skin of a host via a disposable housing (not shown). The system includes a transcutaneous analyte sensor 102 and a transmitter/sensor electronics unit 104 for wirelessly transmitting analyte information to a receiver. In alternative embodiments, the sensor may be non-invasive.

During use, a sensing portion of the sensor 102 is under the host's skin, and a contact portion of the sensor 102 is electrically connected to the electronics unit 104. The electronics unit 104 engages a housing (not shown), and the sensor extends through the housing. The housing, which maintains the assembly 100 on the skin and provides for electrical connection of the sensor 102 to sensor electronics provided in the electronics unit 104, is attached to an adhesive patch fastened to the skin of the host.

The on-skin sensor assembly 100 may be attached to the host with an applicator (not shown) adapted to provide convenient and secure application. Such an applicator may also be used for attaching the electronics unit 104 to a housing, inserting the sensor 102 through the host's skin, and/or connecting the sensor 102 to the electronics unit 104. Once the electronics unit 104 is engaged with the housing and the sensor 102 has been inserted and is connected to the electronics unit 104, the applicator detaches from the sensor assembly.

In general, the continuous analyte sensor system 100 includes any sensor configuration that provides an output signal indicative of a concentration of an analyte. The output signal, which may be in the form of, for example, sensor data, such as a raw data stream, filtered data, smoothed data, and/or otherwise transformed sensor data, is sent to the receiver, which is described in more detail below. In one embodiment, the analyte sensor system 100 includes a transcutaneous glucose sensor, such as that described in U.S. Patent Application Publication No. 2011/0027127, for example, which is incorporated by reference herein in its entirety. In some embodiments, the sensor system 100 includes a subcutaneous glucose sensor, such as that described in U.S. Pat. No. 6,579,690 to Bonnecaze et al. or U.S. Pat. No. 6,484,046 to Say et al., for example. In some embodiments, the sensor system 100 includes a continuous, refillable, subcutaneous glucose sensor, such as that described in U.S. Pat. No. 6,512,939 to Colvin et al., for example. In some embodiments, the sensor system 100 includes a continuous intravascular glucose sensor, such as that described in U.S. Pat. No. 6,477,395 to Schulman et al., or U.S. Pat. No. 6,424,847 to Mastrototaro et al., for example. Other signal processing techniques and glucose monitoring system embodiments suitable for use with the present embodiments are described in U.S. Patent Application Publication Nos. 2005/0203360 and 2009/0192745, both of which are incorporated herein by reference in their entireties.

In some embodiments, the sensor 102 extends through a housing (not shown), which maintains the sensor on the skin and provides for electrical connection of the sensor to sensor electronics, provided in the electronics unit 104. In one embodiment, the sensor 102 is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments the smallest dimension of the elongated conductive body is less than about 0.1 inches, 0.075 inches, 0.05 inches, 0.025 inches, 0.01 inches, 0.004 inches, or 0.002 inches. Preferably, a membrane system is deposited over at least a portion of electroactive surfaces of the sensor 102 (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface.

In general, the membrane system includes a plurality of domains, for example, an electrode domain, an interference domain, an enzyme domain (for example, including glucose oxidase), and a resistance domain, and can include a high oxygen solubility domain, and/or a bioprotective domain, such as is described in more detail in U.S. Patent Application Publication No. 2005/0245799. The membrane system may be deposited on the exposed electroactive surfaces using known thin film techniques (for example, spraying, electrodepositing, dipping, or the like). In one embodiment, one or more domains are deposited by dipping the sensor into a solution and drawing out the sensor at a speed that provides the appropriate domain thickness. However, the membrane system can be disposed over (or deposited on) the electroactive surfaces using any known method.

In the illustrated embodiment, the electronics unit 104 is releasably attachable to the sensor 102, which together form the on-skin sensor assembly 100. The electronics unit 104 includes electronic circuitry associated with measuring and processing the continuous analyte sensor data, and is configured to perform algorithms associated with processing and calibration of the sensor data. For example, the electronics unit 104 can provide various aspects of the functionality of a sensor electronics module as described in U.S. Patent Application Publication No. 2009/0240120, which is incorporated herein by reference in its entirety. The electronics unit 104 may include hardware, firmware, and/or software that enable measurement of levels of the analyte via a glucose sensor, such as the analyte sensor 102. For example, the electronics unit 104 can include a potentiostat, a power source for providing power to the sensor 102, other components useful for signal processing and data storage, and preferably a telemetry module for one- or two-way data communication between the electronics unit 104 and one or more receivers, repeaters, and/or display devices, such as the devices 110-113. Sensor electronics within the electronics unit 104 can be affixed to a printed circuit board (PCB), or the like, and can take a variety of forms. For example, the electronics can take the form of an integrated circuit (IC), such as an application-specific integrated circuit (ASIC), a microcontroller, and/or a processor. The electronics unit 104 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, and the like. Examples of systems and methods for processing sensor analyte data are described in more detail herein and in U.S. Pat. Nos. 6,931,327, 7,310,544 and in U.S. Patent Application Publication Nos. 2005/0043598, 2007/0032706, 2007/0016381, 2008/0033254, 2005/0203360, 2005/0154271, 2005/0192557, 2006/0222566, 2007/0203966 and 2007/0208245, each of which is incorporated herein by reference in its entirety.

One or more repeaters, receivers and/or display devices, such as a key fob repeater 110, a medical device receiver 111, a smart phone 112, a portable or tablet computer 113, and the like are operatively linked to the electronics unit 104. The repeaters, receivers and/or display devices receive data from the electronics unit 104, which is also referred to as the transmitter and/or sensor electronics body herein. In some embodiments the repeaters, receivers and/or display devices transmit data to the electronics unit 104. For example, the sensor data can be transmitted from the sensor electronics unit 104 to one or more of the key fob repeater 110, the medical device receiver 111, the smart phone 112, the portable or tablet computer 113, and the like. In one embodiment, a display device includes an input module with a quartz crystal operably connected to a radio-frequency (RF) transceiver (not shown) that together function to transmit, receive and synchronize data streams from the electronics unit 104. However, the input module can be configured in any manner that is capable of receiving data from the electronics unit 104. Once the data stream is received, the input module sends it to a processor that processes the data stream, such as described in more detail below. The processor is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. The processor includes hardware that performs the processing described herein. Read-only memory (ROM) provides permanent or semi-permanent storage of data, storing data such as a sensor ID, a receiver ID, and programming to process data streams (for example, programming for performing estimation and other algorithms described elsewhere herein). Random access memory (RAM) stores the system's cache memory and is used in data processing. An output module, which may be integral with and/or operatively connected with the processor, includes programming for generating output based on the sensor data received from the electronics unit (and any processing that incurred in the processor).

In some embodiments, analyte values are displayed on a display device. In some embodiments, prompts or messages can be displayed on the display device to convey information to the user, such as reference outlier values, requests for reference analyte values, therapy recommendations, deviation of the measured analyte values from the estimated analyte values, or the like. Additionally, prompts can be displayed to guide the user through calibration or troubleshooting of the calibration.

Additionally, data output from the output module can provide wired or wireless, one- or two-way communication between the receiver and an external device. The external device can be any device that interfaces or communicates with the receiver. In some embodiments, the external device is a computer, and the receiver is able to download current and/or historical data for retrospective analysis by a physician, for example. In some embodiments, the external device is a modem, and the receiver is able to send alerts, warnings, emergency messages, or the like, via telecommunication lines to another party, such as a doctor and/or a family member. In some embodiments, the external device is an insulin pen or insulin pump, and the receiver is able to communicate therapy recommendations, such as an insulin amount and a time to the insulin pen or insulin pump. The external device can include other technology or medical devices, for example pacemakers, implanted analyte sensor patches, other infusion devices, telemetry devices, or the like. The receiver may communicate with the external device, and/or any number of additional external devices, via any suitable communication protocol, including radio frequency (RF), Bluetooth, universal serial bus (USB), any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, and/or a proprietary communication protocol.

System Calibration

When a new sensor of a continuous blood analyte monitor is implanted, it is calibrated to convert an analog or digital signal directly related to the measured analyte from the analyte sensor (e.g., current) to concentration in clinical units for outputting meaningful data to a user. Calibration of commercially available glucose monitors typically involves obtaining one or more reference analyte values. A reference analyte value refers to an analyte value obtained from a self-monitored blood analyte test. One such test is a finger stick test, in which the user obtains a blood sample by pricking his or her finger, and tests the sample using any known analyte sensor. Where the analyte being sampled is glucose, the obtained value is referred to as a blood glucose (BG) value. The BG value is compared to a measurement of glucose taken by the implanted sensor at substantially the same time as the finger stick sample was obtained. During the early stages after sensor implantation, it is expected that baseline and/or sensitivity values may change between sensor calibrations. Thus, as time passes after a calibration using one or more reference values, the resulting calculated sensor values (using a particular conversion function determined at the calibration) may differ from substantially time-corresponding BG values due to changes of the sensor and/or its surrounding environment. This phenomenon is referred to as "drift," and is discussed in more detail below. To provide more accurate sensor values between calibrations, drift is preferably taken into consideration by applying appropriate compensation.

A sensor's sensitivity to analyte concentration during a sensor session can often change as a function of time. This change in sensitivity can manifest itself as an increase in current for a particular level of glucose. In some embodiments, the sensitivity increases during the first 24-48 hours with a relative change in tens of percents. In order to provide an accurate analyte concentration reading to a user, reference meters (e.g., strip based blood glucose measurements) may system calibrations using be needed. Typically, the rate of calibrations can be 1, 2 or more calibrations a day.

In light of the foregoing, a first calibration of a newly implanted sensor is typically performed at a set interval after implantation. This interval, which may be, for example, two hours, avoids calibrating during a time when sensor readings are likely to be too inaccurate to provide meaningful information. Subsequent calibrations are then typically performed at set intervals, such as every four, six, twelve, twenty-four, thirty-six, forty-eight or seventy-two hours, for example. However, the analyte values displayed to the user by the continuous monitor are updated much more frequently, such as, for example, every five minutes. Thus, to compensate for sensor drift that occurs between calibrations, a drift compensation function may be applied to the analyte values calculated by the continuous monitor at regular intervals. That is, the drift behavior of the sensor over time can be measured or predicted and compensated for on a substantially continuous basis. This concept is discussed in more detail below.

Time-Dependent Algorithms

Figure 2:
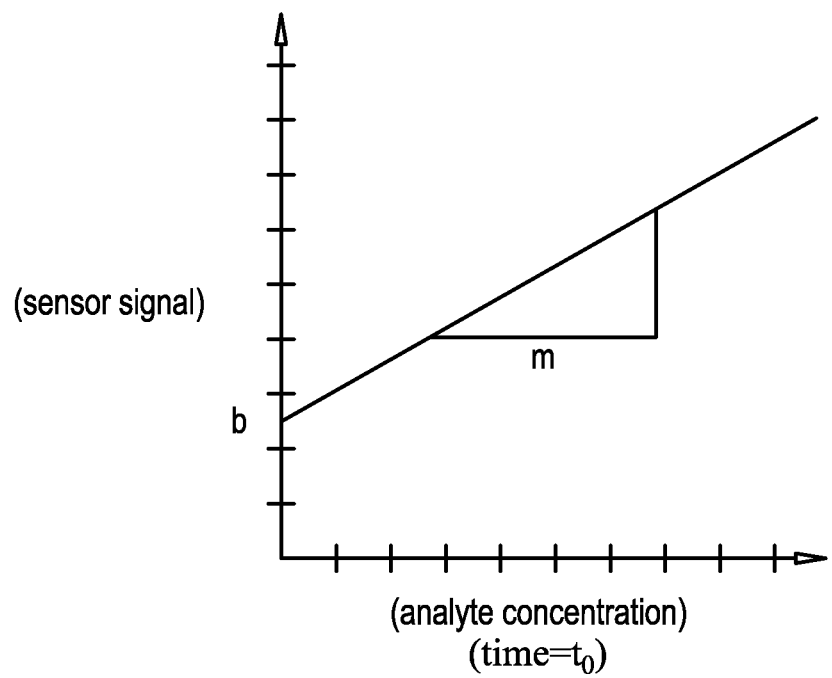
FIG. 2 is a graph illustrating a relationship between analyte concentration and a signal from a continuous analyte sensor at time=$t_0$.
Figure 3:
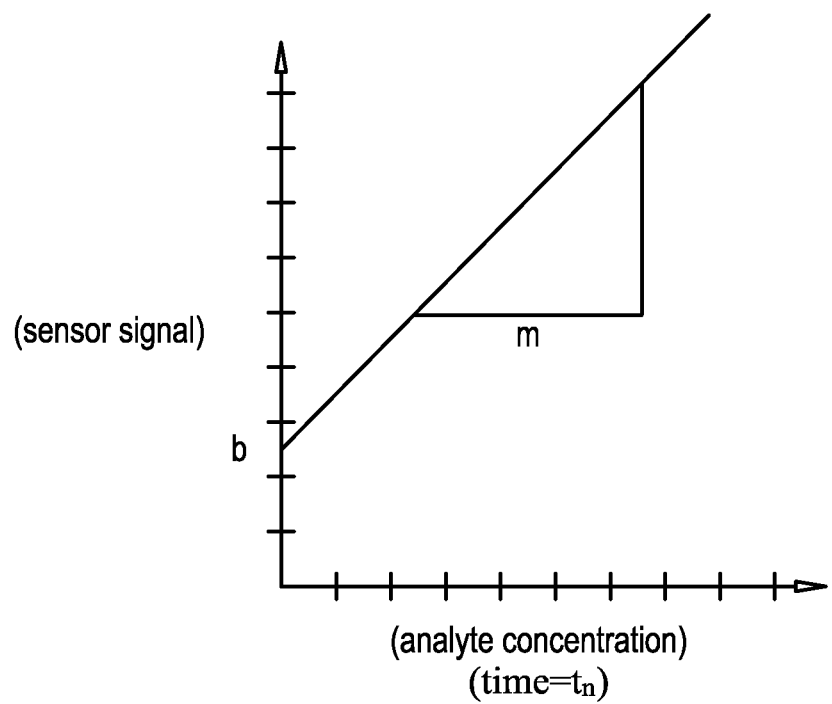
FIG. 3 is a graph illustrating a relationship between analyte concentration and a signal from the continuous analyte sensor at time=$t_n$.

As discussed above, the sensor outputs a signal in the form of electrical current. A conversion function is applied to the sensor signal in order to produce a user output that the user understands as representative of a concentration of analyte in his or her bloodstream. However, the proper conversion function to be applied can be dependent upon an elapsed time since the sensor was implanted. This phenomenon is due to the fact that the sensor may undergo a time-dependent shift in baseline and/or sensitivity after implantation, also referred to as "drift." That is, the baseline and/or sensitivity of the sensor may have a different value at time $t_0$ (at or shortly after implantation) than at time $t_n$ (at a given interval after time $t_0$). Using sensitivity as an example, FIG. 2 illustrates the sensitivity, m, for a given sensor at time $t_0$, while FIG. 3 illustrates the sensitivity, m', for the same sensor at time $t_n$. A comparison of these figures shows that the sensitivity of the sensor (the slope of the curve) has increased from time $t_0$ to time $t_n$. This behavior is typical of some continuous analyte sensors in the early stages after implantation, and can be referred to as "upward signal decay." However, the sensor behavior illustrated in FIGS. 2 and 3 is just one example. Drift can be either upward or downward, and may occur at either the beginning or end of a sensor's lifespan.

Figure 4:
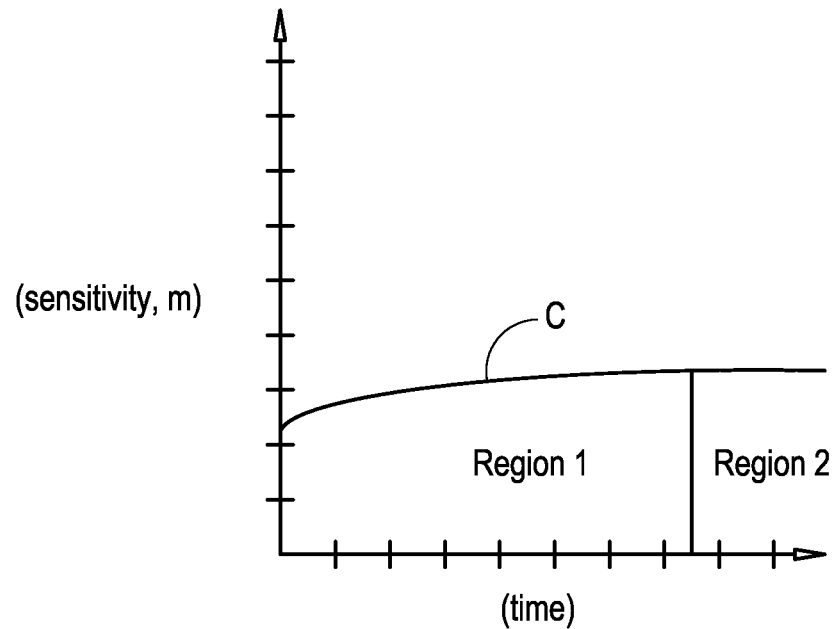
FIG. 4 is a graph illustrating sensitivity of a continuous analyte sensor over time.

FIG. 4 illustrates sensor sensitivity over time in one example sensor, which can be referred to as a sensitivity profile and/or a drift curve. As shown in Region 1 of the drift curve C toward the left-hand side of the graph, the rate of increase in sensor sensitivity is greatest in the early stages after implantation. Region 1 typically spans the first day up to about three days after sensor implantation, but could last more time or less time. For example, Region 1 may span the first six, eight, ten, twelve, eighteen, twenty-four, thirty-six, forty-eight, seventy-two or ninety-six hours after implantation. Eventually, the sensor sensitivity levels off, as shown in Region 2 of the drift curve C. While not shown in FIG. 4, beyond Region 2 the sensor sensitivity begins to decrease as the sensor reaches the end of its usable life.

Figure 5:
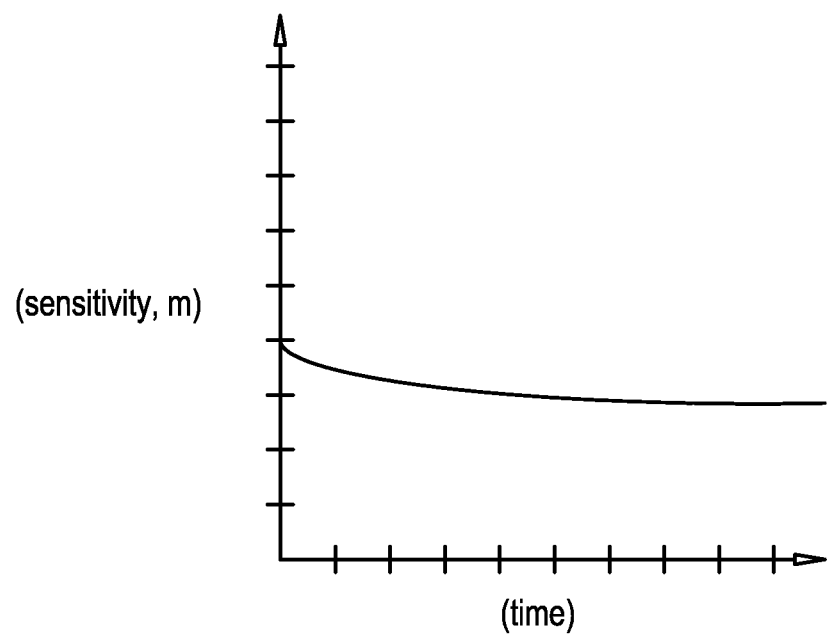
FIG. 5 is a graph illustrating a drift compensation function for the curve shown in FIG. 4.
Figure 6:
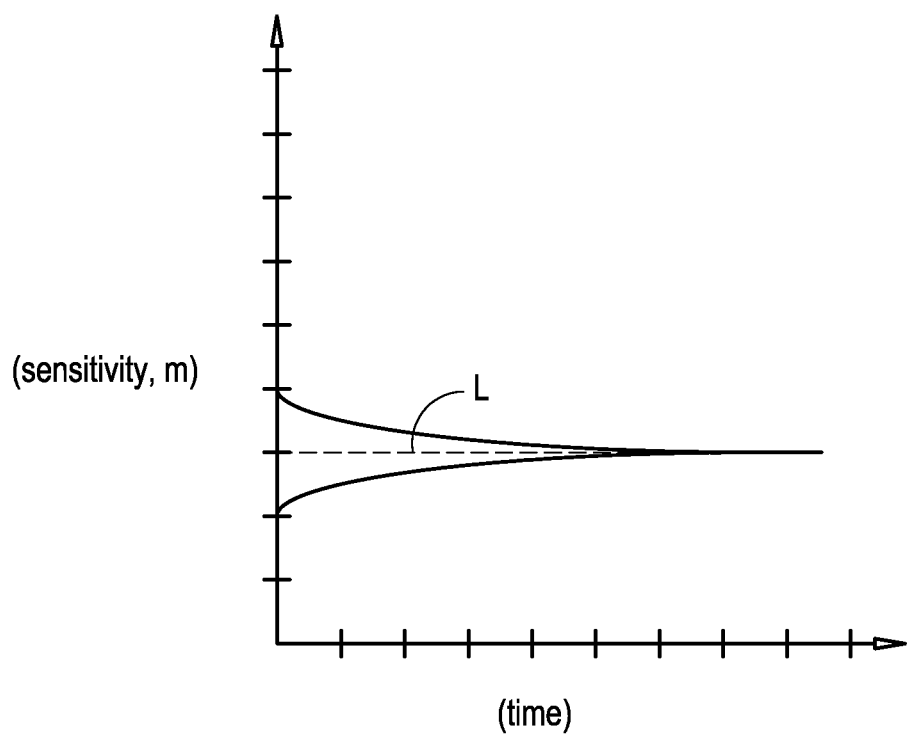
FIG. 6 is a graph superimposing the curves shown in FIGS. 4 and 5.

FIG. 5 illustrates the ideal compensation function for the sensitivity profile, or drift curve, of FIG. 4. It is the ideal compensation function in the sense that it is the inverse of the drift curve of FIG. 4. Thus, when the two curves are superimposed, as in FIG. 6, they resolve to a straight horizontal line L, which exhibits no drift.

Due to sensor drift, application of the proper compensation function depends upon where the sensor is along the drift curve C in FIG. 4. But this factor cannot be determined with absolute certainty, due to the possibility that a sensor may be reused. Typically, at the end of the intended use timeline for a given sensor, the sensor electronics stop the sensor session and the user is instructed to replace the sensor. Hosts, however, often do not replace the sensor for a variety of reasons, including a desire to avoid having to purchase new sensors. Also, a host may remove a sensor before it has reached the end of its life cycle for a variety of reasons, such as a desire to avoid getting it wet while bathing.

Thus, some hosts may restart an old sensor by, for example, pressing a restart button on the sensor electronics, detaching and reattaching the sensor electronics and/or by selecting to "start" a new session from a menu or another user interface-driven methodology. By restarting a sensor that is already implanted, the sensor electronics are under the false assumption that the current sensor has just been implanted for the first time, when in reality it has been in the host's body for a potentially significant amount of time. Certain of the present embodiments provide methods for determining whether the user has implanted a new sensor or restarted an old one. Certain others of the present embodiments provide methods for determining a proper compensation function to be applied to sensor data, taking into account the possibility that a recently implanted sensor may have been restarted. Certain others of the present embodiments provide methods for applying a first compensation function to sensor data during a first interval, and applying a second compensation function to sensor data during a second interval after the first interval.

Figures 7, 7A:
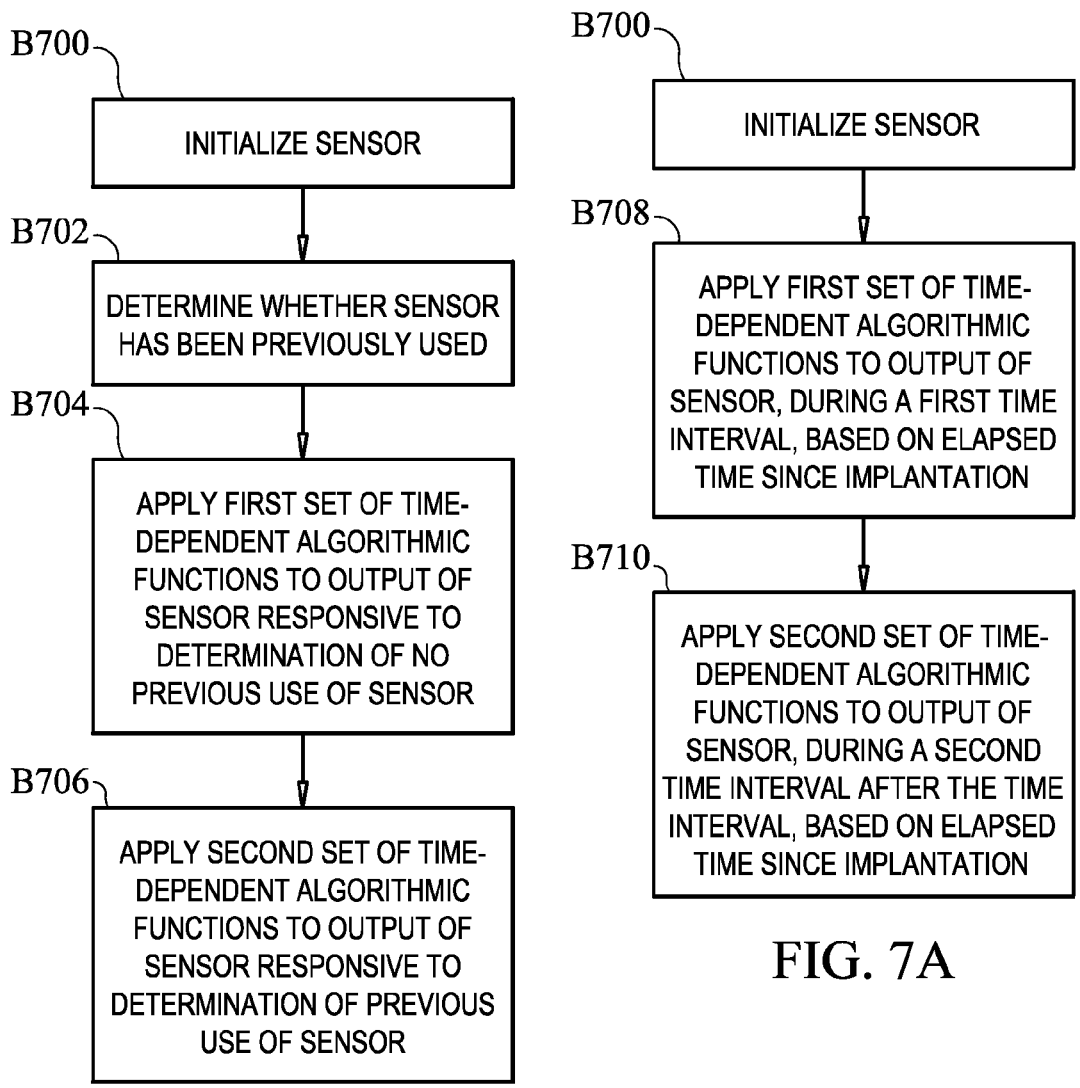
FIG. 7 is a flowchart illustrating a process for applying time-dependent algorithmic functions to sensor data, in accordance with the present embodiments.
FIG. 7A is a flowchart illustrating a process for applying time-dependent algorithmic functions to sensor data, in accordance with the present embodiments.

Certain of the present embodiments comprise systems and methods for processing sensor data of a continuous analyte sensor implanted within a body. With reference to FIG. 7, one embodiment of the present methods comprises initializing the sensor, at B700, and determining whether the sensor has been previously used, at B702. If the sensor has not been previously used, a first set of time-dependent algorithmic functions is applied to an output of the sensor, at B704. If the sensor has been previously used, a second set of time-dependent algorithmic functions is applied to the output of the sensor, at B706. It should be noted that although the time-dependent algorithmic functions may be applied to an output of the sensor, the time-dependent functions also may be applied to any data associated with the sensor, including sensor values, reference glucose values, or the parameters in the linear model, for example.

In one embodiment, determining whether the sensor has been previously used comprises determining a time, delta T, since the prior sensor session ended and the current sensor session was initialized. If t is less than a threshold value, it is determined that the sensor has not been previously used. However, if t is greater than the threshold value, it is determined that the sensor has been previously used. In certain embodiments, initialization times can be stored in memory accessible by the sensor electronics.

In some embodiments, determining whether the sensor has been previously used comprises measuring a change in impedance of the sensor over a time T. With some sensors, it is expected that the impedance of the sensor will change during the early stages after implantation, after which it will level off. The impedance may increase or decrease, depending upon the sensor's characteristics. Thus, if the measured impedance change is greater than a threshold value, it is determined that the sensor has not been previously used. However, if the measured impedance change is less than the threshold value, it is determined that the sensor has been previously used.

One aspect of determining whether the sensor has been reused may be determining the time since it was implanted. Thus, with reference to FIG. 7A, some embodiments of the present methods comprise initializing the sensor, at B700. At B708, a first set of time-dependent algorithmic functions is applied to the output of the sensor, during a first time interval, based on the elapsed time since the sensor was implanted. At B708, a second set of time-dependent algorithmic functions is applied to the output of the sensor, during a second time interval after the first time interval, based on the elapsed time since the sensor was implanted. It should be noted that although the time-dependent algorithmic functions may be applied to an output of the sensor, the time-dependent functions also may be applied to any data associated with the sensor, including sensor values, reference glucose values, or the parameters in the linear model, for example.

For example, after a sensor calibration is performed, a first compensation function may be applied to sensor data for a first time interval. At the end of the first time interval, another sensor calibration is performed. That calibration may indicate that the first compensation function is no longer appropriate, because the sensor signal has drifted. Thus, a second, more appropriate, compensation function may thereafter be applied to sensor data over a second time interval.

As discussed above, in alternative embodiments the sensor may be non-invasive. Thus, in such embodiments, a first set of time-dependent algorithmic functions may be applied to the output of the sensor, during a first time interval, based on the elapsed time since the sensor was first initialized. Then, a second set of time-dependent algorithmic functions may be applied to the output of the sensor, during a second time interval after the first time interval, based on the elapsed time since the sensor was first initialized. It should be noted that although the time-dependent algorithmic functions may be applied to an output of the sensor, the time-dependent functions also may be applied to any data associated with the sensor, including sensor values, reference glucose values, or the parameters in the linear model, for example.

Initializing the Sensor

The present embodiments contemplate numerous techniques for initializing the sensor. For example, initialization may be triggered when the sensor electronics engages the sensor. In another example, initialization may be triggered by a mechanical switch, such as a switch (not shown) on a snap-in base that receives the sensor electronics. When the sensor electronics are snapped into the base, the switch is automatically tripped. In another example, initialization may be menu driven, as the user may be prompted by a user interface to begin initialization by making a selection on the user interface, such as by pushing a button or touching a designated area on a touch screen. In another example involving a non-invasive sensor that is applied to the wearer's skin, the sensor may sense when it is in contact with skin and start automatically.

Determining Whether the Sensor has been Previously Used

The present embodiments contemplate numerous techniques for determining whether the initialized sensor is a new sensor, i.e. one that has never been used before, or a previously used sensor that has been restarted.

In some embodiments, the system is programmed to algorithmically identify a new sensor insertion by looking for changes in signal characteristics (e.g., a spike indicating a break-in period, no change in sensor count values during the first hour, or the like). The frequency or spectral content of the raw signal can be analyzed, for example, to identify electrochemical break-in, and the like.

Another technique may rely on an elapsed time since a previous sensor was removed from the body. The longer the interval between a first sensor being removed and second sensor being implanted, the more likely it is that the second sensor is new.

To measure this interval, the sensor electronics may include hardware and/or circuitry to detect removal of a first (previous) sensor at time $t_0$, implantation of a second (subsequent) sensor at time $t_n$ (where the first and second sensors may be the same sensor), and a timer configured to measure the time elapsed between time $t_0$ and $t_n$. The timer may be started upon detection of the removal of the first sensor, and stopped upon detection of implantation of the second sensor. The elapsed time may then be used to determine whether the second sensor is a new sensor or not.

In some embodiments, the system may rely on user input. For example, when a new sensor is implanted, or an old sensor is restarted, a new sensor session begins. When a user begins a new sensor session, he or she may be prompted to confirm whether or not the sensor is new. The prompt may comprise, for example, a question presented on a graphical user interface.

In some embodiments, the system may require the input or reading of a unique identifier for the sensor. For example, when a user begins a new sensor session, he or she may be prompted to input a unique serial number associated with the sensor into the user interface. The system may be configured to allow only one use of each sensor, so that if the serial number input by the user has been previously input, the sensor electronics may determine that that sensor has been previously used. In such a situation, the sensor electronics may be programmed to not initiate a new sensor session until a new sensor is implanted. Used sensors would thereby be rendered inoperable, because they could not be reused with the sensor electronics.

In an alternative embodiment, each sensor may include a unique identifier that the sensor electronics can read without any need for user input, such as a radio frequency identifier (RFID). When a new sensor session begins, a reader associated with the sensor electronics may read the RFID in order to determine whether a sensor with the same RFID has been previously used. Again, if the sensor has been previously used the sensor electronics may not initiate a new sensor session until a new sensor is implanted.

In some embodiments, the system may compare a calibration line of the sensor with a calibration line of a most recently used sensor. For example, when a new sensor session begins an initial calibration of the sensor is performed. At that time, the user may be prompted by the user interface to input one or more reference analyte values into the sensor electronics. These reference analyte values are used to determine a calibration line for the new sensor session. The new calibration line is then compared to a calibration line drawn at the end of the previous sensor session (old calibration line). If the old and new calibration lines substantially correspond, it is highly probable that the sensor was restarted.

Figure 8:
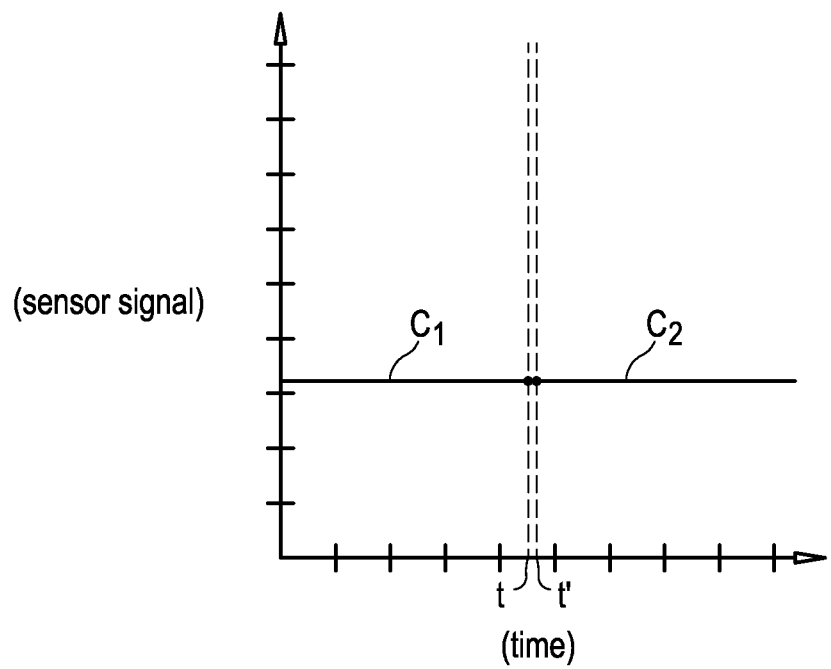
FIG. 8 is a graph illustrating a signal of a continuous analyte sensor over time, and a signal of the same continuous analyte sensor over time after it is reinitialized.

In some embodiments, the system may compare a signal from the sensor with a signal from a most recently used sensor, particularly if a short period of time elapses in between sensor removal and implantation. For example, and with reference to FIG. 8, the curve $C_1$ represents the sensor signal from a mature sensor, i.e. one that has been implanted for a sufficient length of time that its signal does not exhibit substantial drift. The sensor is removed at time t. Shortly thereafter, at time t', a "new" sensor is implanted, and its signal is shown by the curve $C_2$. This sensor signal corresponds to that of the removed sensor, in that it also does not exhibit substantial drift. It is thus highly probable that the old sensor was restarted, because new sensors typically exhibit substantial drift in the early stages after implantation.

Figure 9:
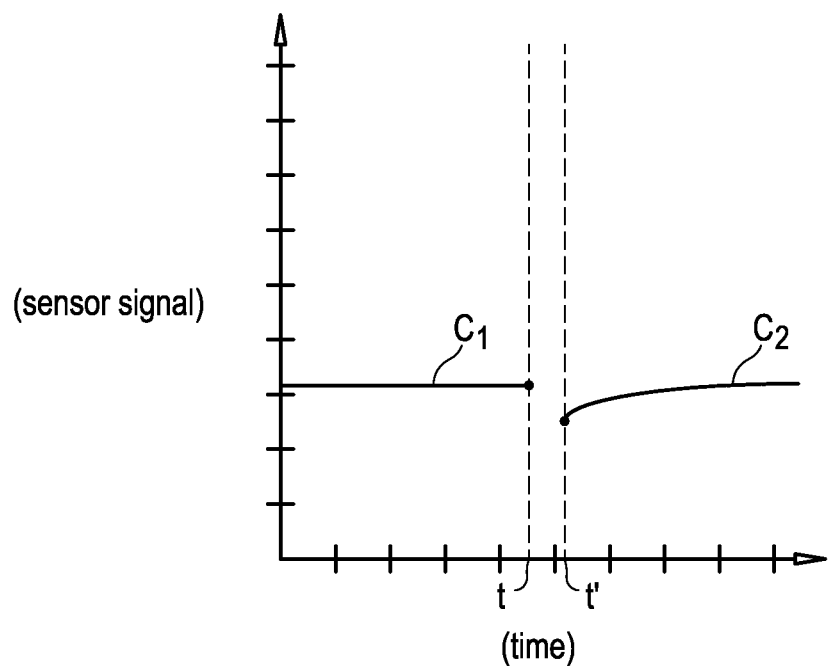
FIG. 9 is a graph illustrating a signal of a first continuous analyte sensor over time, and a signal of a second continuous analyte sensor after the first continuous analyte sensor is removed and the second continuous analyte sensor is implanted.

FIG. 9, by contrast, illustrates a comparison between the signals from a removed sensor and a new sensor. The curve $C_1$ again represents the sensor signal from a mature sensor. The sensor is removed at time t. Some time thereafter, and after a longer interval than that illustrated in FIG. 8, at time t', a new sensor is implanted, and its signal is shown by the curve $C_2$. Because the new sensor has not been reused, its signal exhibits the upward drift that is characteristic of new sensors.

In some embodiments, the system may measure impedance to detect settling of the sensor that results from electrochemical break-in of analyte to the sensor. As used in this application, the term impedance includes resistance, reactance, or any parameters derived from resistance and reactance, such as phase, and may be measured at different frequencies of current. As discussed above, upon implanting a new sensor tissue begins to grow around and within the sensor. As this tissue ingrowth proceeds, impedance of the sensor may increase or decrease. Thus, to determine whether an implanted sensor is a new sensor or one that is being reused, some embodiments apply one or more stimulus signals to the sensor to determine its impedance. As discussed further below, a stimulus signal may be any signal (e.g., any time-varying or spatial-varying quantity, such as an electric voltage, current or field strength) applied to the sensor to elicit a response. Non-limiting examples of stimulus signals that can be used in the embodiments described herein can be a waveform including one or more of: a step increase in voltage of a first magnitude, a step decrease in voltage of a second magnitude (where the first and second magnitudes can be the same or different), an increase in voltage over time at first rate, a gradual decrease in voltage over time having a second rate (where the first rate and the second rate can be different or the same), one or more sine waves overlayed on the input signal having the same or different frequencies and/or amplitudes and the like. A response to the stimulus signal can then be measured and analyzed (the response is also referred to herein as the "signal response"). Based on the calculated impedance value, a determination can be made as to whether the sensor is new or not based on an expected impedance value for a new sensor.

Figure 10:
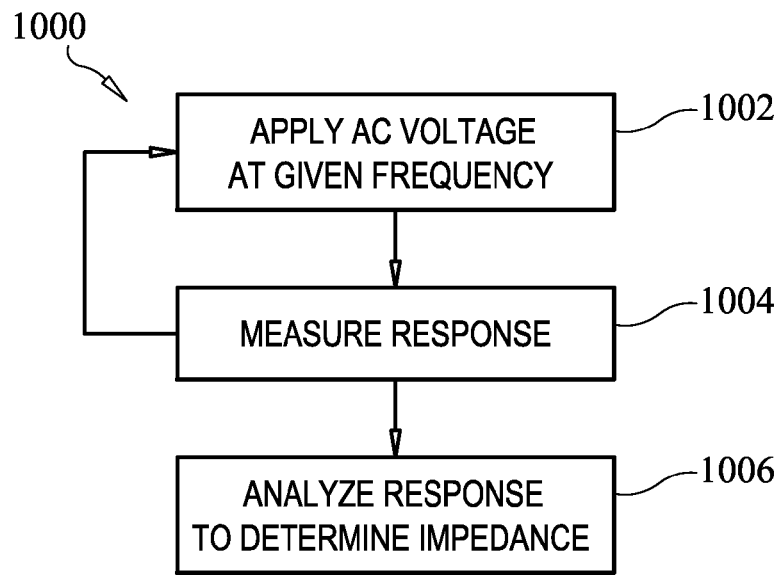
FIG. 10 is a flowchart illustrating a process for determining an impedance of a sensor, in accordance with the present embodiments.

FIG. 10 is a flowchart illustrating a process 1000 for determining an impedance of a sensor in accordance with the present embodiments. At step 1002, a stimulus signal in the form of an alternating current (ac) voltage at a given frequency is applied to a working electrode of the sensor being studied. The ac voltage can be overlayed on a bias potential and can be relatively small as compared to the bias potential, such as voltage that is in the range of about 1% to 10% of the bias voltage. In one embodiment, the ac voltage is a sine wave having an amplitude in the range of 10-50 mV and a frequency in the range of between about 100 Hz-1 kHz. The sine wave can be overlayed on a 600 mV bias voltage. The response signal (e.g., in units of current) can then be measured in step 1004 and analyzed in step 1006 to determine an impedance at the given frequency. Should the impedance of the sensor at a range of frequencies be of interest, the process 1000 can be repeated by applying an ac voltage at each frequency of interest and analyzing corresponding output responses.

Figure 11:
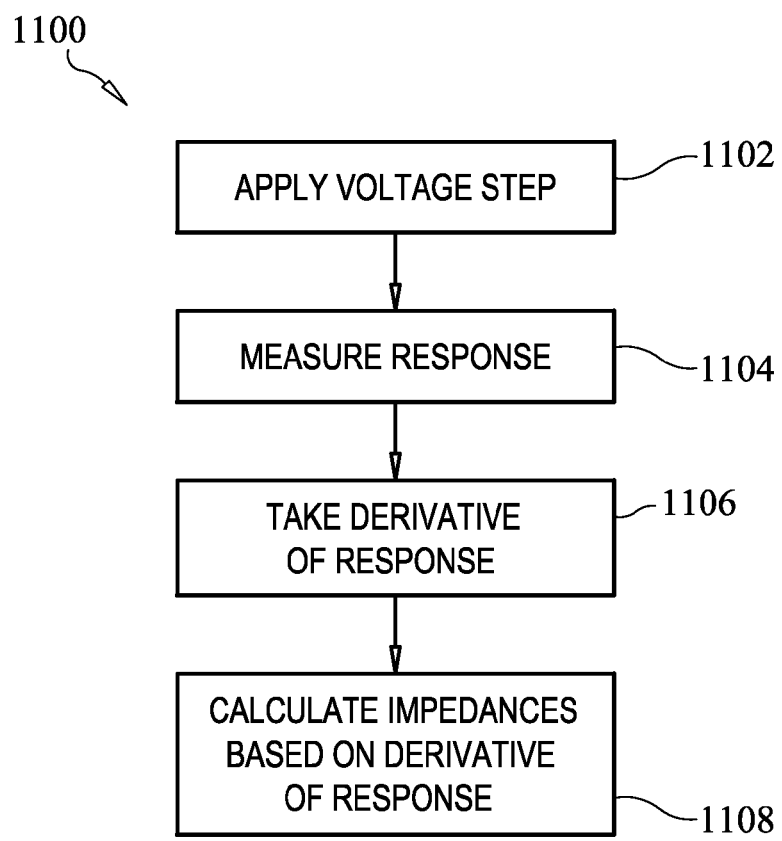
FIG. 11 is a flowchart illustrating a process for determining an impedance or plurality of impedances of a sensor being studied by applying one or more stimulus signals and converting the response signal or signals to a frequency domain, in accordance with the present embodiments.

FIG. 11 is a flowchart illustrating a process 1100 for determining an impedance or plurality of impedances of a sensor being studied by applying one or more stimulus signals and converting the response signal or signals to a frequency domain in accordance with the present embodiments. The data can be converted to the frequency domain using a Fourier transform technique, such as a fast Fourier transform (FFT), discrete time Fourier transform (DTFT) or the like. At step 1102, a stimulus signal in the form of a voltage step can be applied to a bias voltage of the sensor. The voltage step can be in the range of 10-50 mV, for example 10 mV, and the bias voltage can be 600 mV. The signal response can then be measured and recorded (e.g., an output current) at step 1104, and a derivative of the response can be taken at step 1106. At step 1108, a Fourier transform of the derivative of the response can then be calculated to yield ac currents in the frequency domain. One or more impedances of the sensor over a wide spectrum of frequencies can then be calculated based on the ac currents at 1110.

Figure 12:
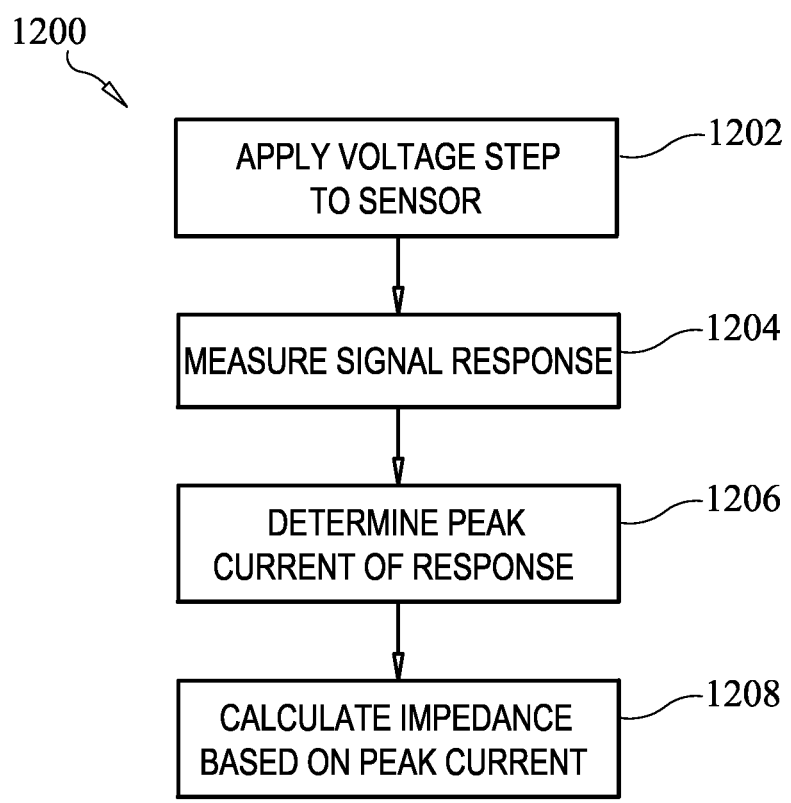
FIG. 12 is a flowchart illustrating a process for determining an impedance of a sensor being studied, in accordance with the present embodiments.

FIG. 12 is a flowchart illustrating a process 1200 for determining an impedance of a sensor being studied, such as the impedance of the sensor's membrane, in accordance with the present embodiments. At step 1202, a stimulus signal in the form of a voltage step above a bias voltage is applied to the sensor. The signal response is measured at step 1204, and, at step 1206, a peak current of the response is determined. Next, at step 1208, impedance (e.g., resistance) of the sensor membrane (e.g., $R_{membrane}$) is calculated based on the peak current. In an alternative embodiment, instead of calculating a sensor impedance based on the peak current, the peak current can be correlated to one or more predetermined sensor relationships to determine a property of the sensor, such as the sensor's sensitivity.

Figure 13A:
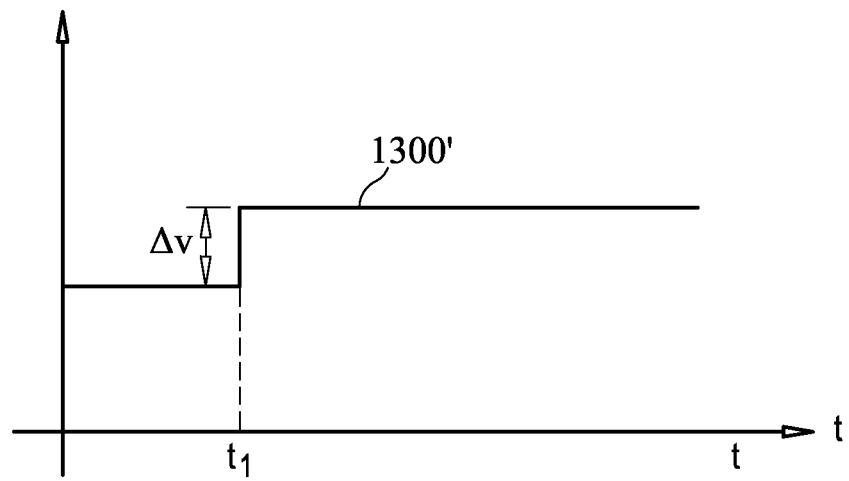
FIG. 13A is a graph of an input voltage applied to an analyte sensor over time, in accordance with the present embodiments.

The relationship between a signal response resulting from a stimulus signal in the form of a voltage step and a sensor membrane resistance of embodiments of analyte sensors will now be discussed further with reference to FIGS. 13A and 13B. FIG. 13A is a graph of an input voltage 1300 applied to an analyte sensor over time in accordance with the present embodiments. The input voltage 1300 applied to the analyte sensor initially corresponds to the bias voltage, which in one embodiment is about 600 mV. A stimulus signal in the form of a voltage step is then applied to the input voltage at time $t_1$. The magnitude of the voltage step, $\Delta v$, can be in the range of 10-50 mV, for example 10 mV.

Figure 13B:
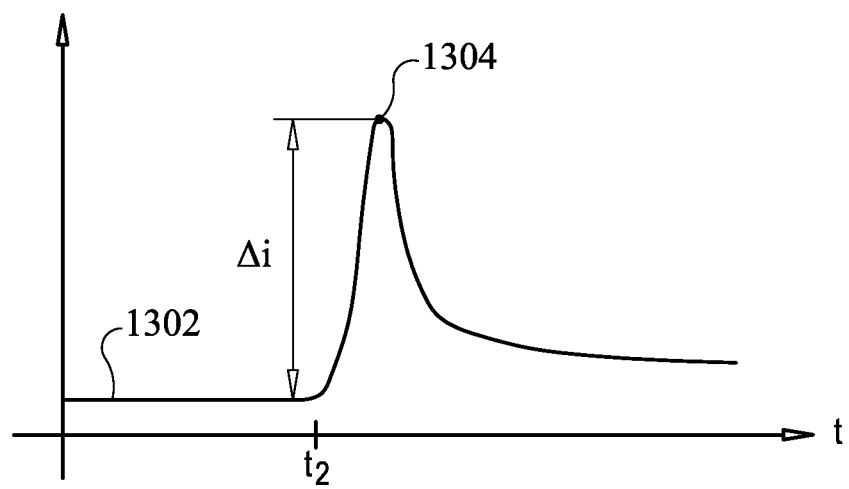
FIG. 13B is a graph of a current response of the analyte sensor to the input voltage of FIG. 13A.

FIG. 13B is a graph of a current response 1302 of the analyte sensor to the input voltage 1300 of FIG. 13A. As illustrated in FIG. 13B, the current response 1402 can include a sharp spike in current starting at time $t_2$, which corresponds to the time in which the voltage step begins to impact the response. The current response 1302 includes a peak current at point 1304 and then the current response 1302 gradually decreases and levels off to a slightly higher level due to the increase in input voltage 1300 as compared to before the voltage step.

In one embodiment, a change in current, $\Delta i$, measured as the difference between the magnitude of the current response 1302 prior to the voltage step and the peak current 1304 resulting from the voltage step, can then be used to estimate the sensor membrane resistance, such as $R_{membrane}$. In one embodiment, an estimated sensor membrane resistance can be calculated using Ohms Law, where $$R_{membrane} = \Delta v / \Delta i$$

As discussed above, $\Delta v$ is the step voltage increase and $\Delta i$ is the change in current response due to the step voltage increase.

In certain embodiments, two or more of the foregoing methods for determining whether a sensor has been previously used may be used together. For example, elapsed time between sensor removal and implantation may be used together with comparing sensor signals. If a short time elapses between sensor removal and implantation, and the signal from the implanted sensor is substantially identical to the signal from the removed sensor, it is highly likely that the old sensor was restarted. In another example, comparing sensor calibration lines may be used together with comparing sensor signals. Again, if both the calibration lines and the sensor signals are substantially identical for the old and new sensors, it is highly likely that the old sensor was restarted. In another example, measuring impedance may be used together with comparing trends in sensor signals. Any of the present methods may be used in combination with any other of the present methods, and any given combination may include two or more distinct methods, such as three or four methods in combination. As more and more methods are combined, the probability of correctly determining whether a sensor is new or has been restarted increases when the results of each method are in agreement.

Various methods may be used to combine the results of multiple methods for determining whether a sensor is new or has been restarted. Examples include weighted averaging and fuzzy logic. These methods are well known, and will not be further elaborated upon here. Another example method is decision fusion. Decision fusion provides a statistical model that combines information from multiple tests and takes into account the performance of each "detector" for prediction of sensor restart. Decision fusion requires that binary decisions ("yes" or "no") are made independently at each detector. These decisions are fused (multiplied) in the form of likelihood values that depend only on the known performance (sensitivity and specificity) of each detector. The result is a fused set of likelihood values that can be compared to a threshold to make a final decision.

The true case of "yes" (sensor restart) is given as $H_1$, and the true case of "no" (new sensor) is given as $H_0$ (i.e. the null hypothesis). Decisions are made for each test (d=1 or d=0) and it is known from previous work what the sensitivity and specificity is for each test. Each decision is then converted to a likelihood value, $\lambda$:

$$\lambda(d) = \frac{P(d|H_1)}{P(d|H_0)}.$$

The likelihood value is the probability of making a decision in the case that the sensor has been restarted, divided by the probability of making a decision in the case that the sensor has not been restarted. For a decision of "yes," or 1, the likelihood value is the probability of detection (Pd) divided by the probability of a false alarm (Pf):

$$\lambda(d) = \frac{P(d|H_1)}{P(d|H_0)} = \begin{cases} \frac{Pd}{Pf} & \text{if } d = 1 \\ \frac{1-Pd}{1-Pf} & \text{if } d = 0. \end{cases}$$

For a test with a high probability of detection and a low probability of false alarm, $\lambda$ will be very high for a decision of 1 and very small for a decision of 0. This is how the weighting of each decision based on test performance comes in. Once each decision is converted to a likelihood value, all the likelihood values are simply multiplied together and the final likelihood value is compared to a threshold to make the final decision.

In some embodiments, the system may apply a voltage to the sensor at the end of a sensor session. The voltage may be high enough to render the sensor in a state in which it is known that the sensor has reached an end of a sensor session. Thus, if the user tries to reuse that sensor, the system will know that the sensor is being reused.

In some embodiments, the system may use sensitivity information (e.g., a sensitivity coefficient (SC) and/or calibration line) from the end of previous sensor session to determine an expected or estimated glucose value (EGV) at the beginning of a subsequent sensor session. Then, the user obtains his or her blood glucose (BG) through a finger stick, or other equivalent method, and the EGV and BG are compared (i.e., at the startup of the subsequent sensor session). If the user had actually inserted a new sensor (rather than attempting to reuse a sensor), then with certain sensor designs that exhibit sensor drift, the EGV should not correspond to the BG because the sensitivity from the end of a previous sensor session should not be the same as the sensitivity from the beginning of a subsequent sensor session, for example, such as described with respect to FIG. 4. Accordingly, if the difference between the BG and the EGV is within a predetermined tolerance, it may be determined that the sensor has been reused, because for sensor designs that exhibit drift in the early stages after implantation the difference between the BG and the EGV should not be within the predetermined tolerance.

In some embodiments, the system may project a future EGV using a glucose trend from the last previous session. The projection may be, for example, at most fifteen minutes into the future. An EGV at the same point in time in the future is then calculated for the current session using a first SC. An error between the projected EGV and the EGV of the new session is then calculated. If the error is within a predetermined tolerance, it may be determined that the sensor has been reused, because for sensors that exhibit drift in the early stages after implantation the error between the projected EGV and the EGV of the new session should not be within the predetermined tolerance.

Applying Time-Dependent Algorithmic Functions Based Upon Determination of Elapsed Time Since Implantation Referring again to FIG. 7A, once the sensor has been implanted and initialized (B700), an appropriate time-dependent algorithmic function, or functions, is/are applied to the sensor data. In this embodiment, first and second function(s) (B708, B710, respectively) to be applied is/are based on the elapsed time since the sensor was implanted, and optionally on a determination as to whether the sensor is new or has been reused.

In one embodiment, drift compensation may be applied based on an elapsed time since implantation, for example where the drift compensation takes into account where along the drift curve (e.g., sensitivity curve) the sensor is. For example, it may be determined that the sensor was in use for one day. The applied drift compensation would take the one day of use into account and apply a drift compensation function that would normally be applied to a one day old sensor, rather than one that would be applied to a new sensor. Accordingly a first drift compensation function (or parameter of that function) is applied at a first elapsed time since implantation and a second drift compensation function (or parameter of that function) is applied at a second elapsed time since implantation.

In some embodiments, the conversion function may be adaptive and comprise two or more different conversion functions, or parameters applied to the conversion function, adaptively applied based on elapsed time since implantation. In one such embodiment, the conversion function may include one or more assumed parameters and/or boundaries, which have values that are dependent on the elapsed time since implantation.

In one example embodiment, the applied conversion function includes predetermined baseline information, which may include a scaling factor to be applied to a calculated or measured baseline, a priori baseline assumptions to be applied to a conversion function, and/or the like, wherein the predetermined baseline information adapts, at least in part, based on elapsed time since implantation. Accordingly, first baseline information (a first algorithmic function) is applied at a first time and second baseline information (a second algorithmic function) is applied at a second elapsed time since implantation. For example, it may be assumed that a sensor has a higher or lower baseline on day three than it does on day one. Thus, once the age of the sensor is known, the applied conversion function may adjust the baseline accordingly. In another example embodiment, the applied conversion function may be subject to boundary tests, such as described in more detail below, wherein the boundaries adapt, at least in part, based on elapsed time since implantation. Accordingly, at a first time after implant, first boundary conditions are provided by the first time-dependent algorithmic function and second boundary conditions are provided by the second time-dependent algorithmic function.

Figure 14:
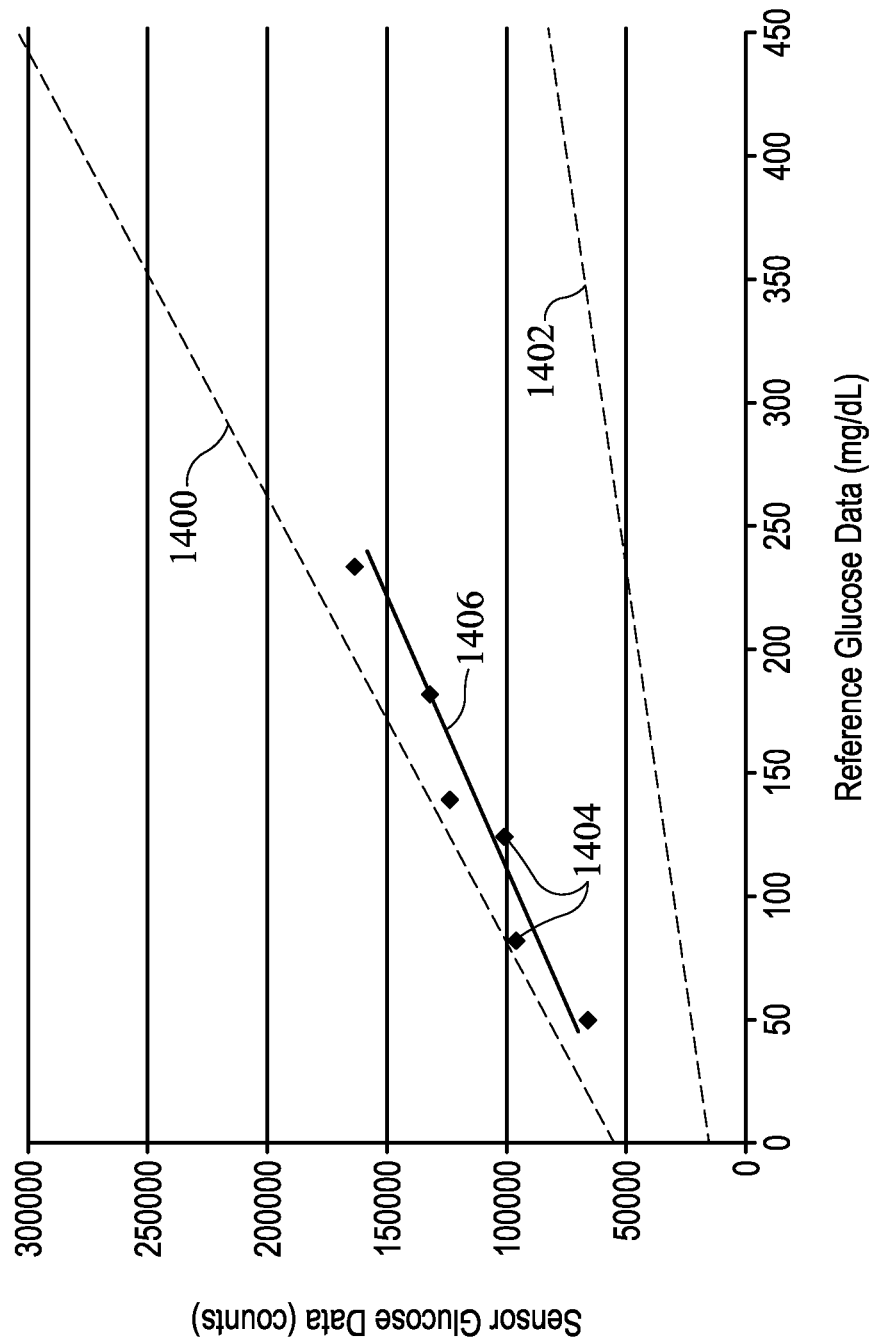
FIG. 14 is a graph that illustrates one example of using prior information for slope and baseline.

FIG. 14 is a graph that illustrates one example of using prior information for slope (sensitivity) and baseline. The x-axis represents reference glucose data (blood glucose) from a reference glucose source in mg/dL. The y-axis represents sensor data from a transcutaneous glucose sensor of the present embodiments in counts (a count is a unit of measurement of a digital signal, which is derived from current from a working electrode of the transcutaneous glucose sensor, in some embodiments). An upper boundary line 1400 is a regression line that represents an upper boundary of "acceptability" in this example. A lower boundary line 1402 is a regression line that represents a lower boundary of "acceptability" in this example. The boundary lines 1400, 1402 were obtained from retrospective analysis of in vivo sensitivities and baselines of glucose sensors as described with respect to the present embodiments. As described above, the boundary lines 1400, 1402 can adaptively adjust, or change, based on the elapsed time since implantation; namely, taking into consideration an expected change in a conversion function over time during implantation associated with changes in baseline and/or sensitivity thereof.

A plurality of matched data pairs 1404 represents data pairs in a calibration set obtained from a glucose sensor as described with respect to the present embodiments. The matched data pairs are plotted according to their sensor data and time-corresponding reference glucose data. A regression line 1406 represents the result of regressing the matched data pairs 1404 using least squares regression. In this example, the regression line falls within the upper and lower boundaries 1400, 1402, thus indicating that the sensor calibration is acceptable. The number of matched data pairs chosen for inclusion in this calibration set may be dependent on elapsed time since implantation, for example, fewer matched data pairs when the conversion function is changing at a faster rate during the first few days after implant, and more matched data pairs when the conversion function is more stable after those first few days.

In some embodiments, if the slope and/or baseline fall outside the predetermined acceptable boundaries described above, which would be illustrated in this graph by a line that crosses the upper and/or lower boundaries 1400, 1402, then the system is configured to assume a baseline value and re-run the regression (or a modified version of the regression) with the assumed baseline, wherein the assumed baseline value is derived from in vivo or in vitro testing. As described above, this assumed baseline may be adaptive based on elapsed time since implantation, for example, a first value on day one, a second value on day two, a third value on day three, or the like. Subsequently, the newly derived slope and baseline are again tested to determine whether they fall within the predetermined acceptable boundaries. Similarly, the processing continues in response to the results of the boundary test. In general, for a set of matched pairs (e.g., calibration set), regression lines with higher slope (sensitivity) have a lower baseline and regression lines with lower slope (sensitivity) have a higher baseline. Accordingly, the step of assuming a baseline and testing against boundaries can be repeated using a variety of different assumed baselines based on the baseline, sensitivity, in vitro testing, and/or in vivo testing. It is preferred that after about two iterations of assuming a baseline and/or sensitivity and running a modified regression, the system assumes an error has occurred (if the resulting regression lines fall outside the boundaries) and fail-safe. The term "fail-safe" includes modifying the system processing and/or display of data responsive to a detected error to avoid reporting of inaccurate or clinically irrelevant analyte values.

As described above, time-dependent boundaries may be applied to the conversion function to provide any number of different algorithmic functions to be applied at any given time after implant. For example, upper and lower boundaries may be applied to limit the conversion function, where the upper and lower boundaries change over time. It is known, for example, that for some sensors sensitivity rises during the first day to three days after implantation, and eventually levels off. It is also known that for some sensors the slope of the sensor drift curve is greatest shortly after implantation, and gradually decreases. Accordingly, the time-dependent algorithmic functions in this case are the boundaries (e.g., lines) that delineate acceptable slopes and baselines of the conversion function. The boundaries may be obtained, for example, from retrospective analysis of in vivo sensitivities and/or baselines of analyte sensors. As this example illustrates, applied a priori knowledge doesn't have to be static. Rather, it can change over time in response to expected and/or measured changes in a given parameter and/or time. Further, applying a priori knowledge dynamically is not limited to the conversion function itself. Namely, adaptive time-based parameters could be applied to any data or processing associated with processing of the continuous analyte data, including sensor sensitivity, sensor baseline, matched data pairs, drift of the sensitivity or baseline over time, etc. For example: boundaries for allowable sensitivity values may change dependent on elapsed time since implantation; boundaries for allowable baseline values may change dependent on elapsed time since implantation; boundaries for allowable deviations of matched data pairs may change based on elapsed time since implantation; boundaries for allowable drift of the sensitivity over time may change based on elapsed time since implantation; and boundaries for allowable drift of baseline over time may change based on elapsed time since implantation. By "change," it is meant that the allowable boundaries may increase, decrease, tighten in range or loosen in range, for example. The adaptive values may change daily in a step-wise fashion or continuously based on a curve or function as may be appreciated by one skilled in the art.

In some embodiments, the number of matched data pairs in the calibration set changes depending upon the elapsed time since implantation as discussed above. For example, for sensors where sensor sensitivity is known to rise during the first day after implantation, and eventually levels off, fewer, or only more recent (e.g., last 1, 2, or 3), matched data pairs may be used in the calibration set during the interval where drift is severe, such as for example ±20%, 10%, 5%, 3%, 2%, 1%. In this embodiment, older data pairs, which are not truly representative of the current state of the sensor due to the severe drift, are discarded so that they do not negatively affect the accuracy of the applied compensation function. By contrast, as the sensor matures and drift levels off, more matched data pairs may be used in the calibration set (e.g., 3, 4, 5, 6, 7, 8 or more).

In some embodiments, fewer sensor calibrations, for example requests for reference data from the user, may be made when drift is minor or nonexistent. Again, it is known that sensor sensitivity rises during the first day after implantation, and eventually levels off. Thus, after the sensitivity levels off there is less of a need for sensor calibrations. If a threshold number of calibrations consistently reveal that little or no drift is occurring, future calibrations may be omitted, or a frequency of calibrations reduced.

In some embodiments, error detection or fail-safes may include parameters that are dependent upon elapsed time since implantation, for example, error detection and/or fail-safes may apply a first set of rules (e.g., more liberal) on day 1 vs. a second set of rules (e.g., more stringent) on days 2 and following. As one example, outlier detection parameters may change over time. An outlier is a reference data point that is very far away from a calculated sensor glucose value (e.g., in a matched data pair). Outlier detection may be applied to raw sensor data, calculated (calibrated) sensor data or both. These data points may be discarded, but over time the criteria for deciding what constitutes an outlier may change. For example, early on after sensor implantation, fewer data points may be classified as outliers, because the sensor is undergoing a large amount of drift. Over time, as drift levels off, reference data points may be more liberally discarded even where they have less variation from sensor glucose value than data points that may not have been discarded earlier in the sensor life cycle.

Any of the above adaptive parameters or processes may be used alone or in combination dependent on the elapsed time since implantation and may further be dependent upon other inputs, such as drift, for example, which is discussed in more detail elsewhere herein.

Drift Compensation

Figure 15:
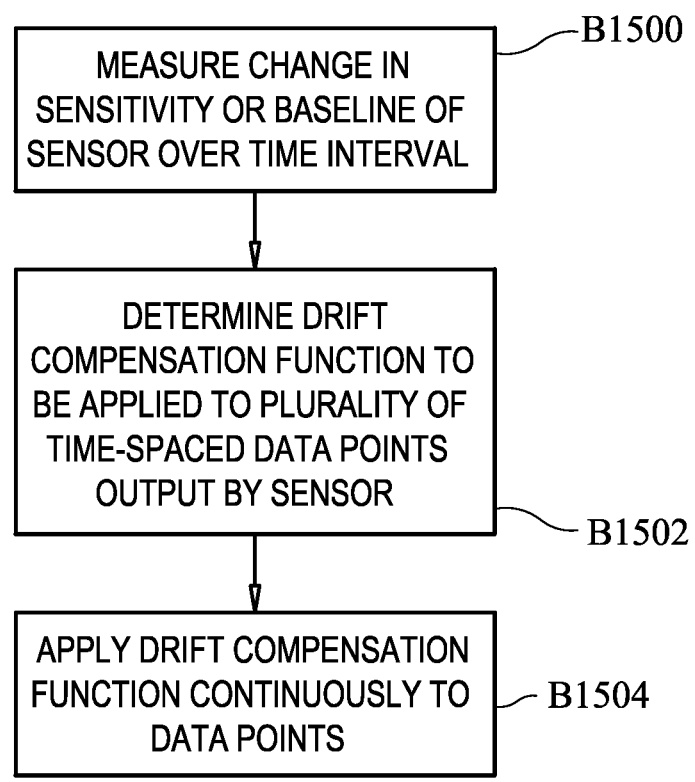
FIG. 15 is a flowchart illustrating a process for applying drift compensation to sensor data, in accordance with the present embodiments.

With reference to FIG. 15, some embodiments of the present methods comprise measuring a change in sensitivity or baseline of a sensor over a time interval, at B1500. It is then determined what drift compensation function is to be applied to a plurality of time-spaced data points output by the sensor, at B1502, and the drift compensation function is then applied continuously (e.g., iteratively) to the data points, at B1504.

In some embodiments, the drift compensation function may be applied not only to the data points output by the sensor, but also to a calibration set (calset) that the sensor uses to produce the data points. The calset is the set of matched pairs of sensor counts to blood glucose values obtained at substantially the same time as each count. The calset is used to draw a calibration line. In these embodiments, the drift compensation function is applied to the sensor counts to scale those counts. For example, the following formula may be used: Counts'= (1+Adjustment)*Counts. The calibration line is then redrawn using the adjusted Counts' values. The counts may be adjusted in real time or retrospectively, for example.

Measuring a Change in Sensitivity and/or Baseline of a Sensor Over a Time Interval In one embodiment, a current sensitivity and/or baseline value of a sensor is compared to a previous sensitivity and/or baseline value of the sensor. For example, a first measured sensitivity or baseline of the sensor may be taken at a beginning of a time interval, and a second measured sensitivity or baseline of the sensor may be taken at an end of the time interval. The first and second measured sensitivities or baselines are then compared to determine whether the sensitivity is increasing, decreasing, or remains stable. The sensitivity may be measured periodically to track a rate of change of the sensitivity. The rate of change can then be used to determine an appropriate drift compensation to be applied to data from the sensor. Measurements may be taken at intervals of any length, such as, for example, every twelve hours.

In some embodiments, the measured change in sensitivity or baseline of the sensor is based on a seed value. A seed value is a predetermined quantity or rate. In the present embodiments, the seed value would thus be a predetermined sensitivity or baseline value or rate of change value of the sensor at time $t_0$. For example, a sensitivity or baseline of a new sensor prior to implantation may be known from, for example, experimental data, product testing, etc., and may be based on a measured absolute impedance of the sensor. The impedance of the sensor, which may be calculated at multiple frequencies, may be measured in vitro or in vivo, and more than one frequency may need to be tested. Also, a typical drift pattern for the sensor may be known from, for example, experimental data, product testing, etc. Comparing a measured sensitivity or baseline of the sensor at time $t_n$ with the predetermined sensitivity or baseline at time $t_0$ provides an estimation of the change in sensitivity or baseline over the interval from $t_0$ to $t_n$. A drift compensation function to be applied to data output from the sensor can then be determined based on the estimated change in sensitivity or baseline. The drift compensation function to be applied is thus based, at least in part, on the predetermined sensitivity or baseline. A value of the predetermined sensitivity and/or baseline may be encoded on electronics associated with the sensor, for example, encoded on sensor packaging (e.g., a cell phone readable QR code, or the like). In addition, other values and/or functions may be encoded on the sensor electronics, such as one or more predicted plateaus, one or more predicted profiles, one or more compensation functions, one or more drift curves, in vitro data, etc.

In some embodiments, the seed value may be generic, or independent of known characteristics of the body in which the sensor is implanted. In alternative embodiments, the seed value may be assigned according to known characteristics of the body in which the sensor is implanted. The characteristics may include, for example, at least one of age, body type, e.g., BMI or percentage body fat, gender, diabetes type, diabetes duration, concomitant diseases (e.g., diabetic nephropathy) and/or sensor location.

In some embodiments, sensitivity seed values may be used to correct and/or direct parameters in the applied compensation function, which is described in more detail elsewhere herein, including drift envelope drift rates (e.g. the max correction rate that can be applied in a given time window), start time of compensation (e.g. the time after sensor insertion that the drift compensation function starts), end time of the drift compensation function, start time of the different time windows in the drift envelope, length of time windows (steps in a stepwise function), or the like, which may be adaptive based on a seed value, a measured drift rate, reliability information, or the like. For example, multiple compensation functions may be available to choose from, and the selection may depend upon the sensitivity seed value. The sensitivity seed value can, in one example, provide the a priori drift rate or magnitude information. The multiple compensations functions may be created to span a range around the seed value. For example, if the seed value for drift magnitude is 50% then the compensation functions could be created with drift magnitudes of 40, 45, 50, 55, and 60% drift magnitudes. In some embodiments, the base compensation function is based on an exponential function or logarithmic function and the multiple compensation functions are generated with a range of time constants indicative of an amount of time for the sensor response to reach some fraction of its stable baseline or sensitivity. For example, if a sensor typically reaches 90% of its final sensitivity within 24 hours then compensation functions could be generated with time constants of 20, 22, 24, 26, and 28 hours. Multiple compensation functions may be derived from in vitro testing, or prior in vivo sessions of a given host. Sensitivity seed values may be determined from prior in vitro testing and/or in vivo testing of sensors on the same host or a similar group of hosts. In one example, sensitivity information from a previous sensor session with a single host is transferred and applied as a seed value to subsequent sensor session(s) of the same host. In some embodiments, the seed value may change based on the sensitivity calculated by the algorithm at the initial calibration. In some embodiments, the seed value may be changed based on the sensitivity value at a calibration.

In some embodiments, a seed value may be encoded on electronics associated with the sensor. For example, some sensors may have known drift profiles and/or known initial sensitivities. Such sensors may include calibration code that includes the appropriate compensation function to be applied to compensate for the known drift profile and/or known initial sensitivity. Drift profiles and/or known initial sensitivities may be determined by an in vitro drift simulation test, or based on actual in vivo testing of similar sensors. In vitro drift simulation tests may be configured to modulate glucose in vitro to simulate in vivo glucose patterns, or the like.

In some embodiments, the measured change in sensitivity or baseline of the sensor is compared to a priori knowledge in order to determine whether a new sensor has been implanted or an old sensor has been restarted. For example, some new sensors exhibit a characteristic upward signal drift in the first few days after implantation, and some new sensors exhibit a characteristic downward signal drift in the first few days after implantation. Thus, in sensors that exhibit upward or downward drift, if a measured change in sensitivity of that sensor shows the expected drift (upward or downward), then it is likely that the sensor is new. But, if the measured change in sensitivity of that sensor shows no drift, or drift in the direction opposite from that expected, then it is likely that the sensor has been restarted. A priori knowledge can also be used to detect other conditions besides sensor restart, such as whether or not a sensor is faulty, for example.

In one example, drift rate is calculated by taking the difference between an estimated blood glucose value (EGV) and a reference blood glucose value (BG), and dividing the result by the time since the continuous blood glucose monitor was last calibrated. EGV is based on sensor data that has already been converted using a previous calibration (conversion function). The BG value is obtained with a self-monitoring test, such as a finger stick. As with previous examples, the calculated drift rate may be bound by a priori knowledge and may change over time as described in more detail elsewhere herein. For example, over time the drift rate for a newly implanted sensor that exhibits characteristic drift should decrease. Thus, if a drift rate calculation indicates that the drift rate is not decreasing, it may be determined that the sensor has been restarted, or is faulty. It is noted that the drift rate may be calculated only when the last calibration was at least 2, 3, 4 or more hours previous to the current calibration in some embodiments due to the slow change of drift.

In another example, drift rate may be filtered or smoothed, for example estimated based on a weighted average of a current drift rate and at least one previous drift rate. This example can be illustrated as:

$$\text{drift}_{estimate} = (1-n)\text{drift}_{old} + n(\text{drift})_{measurement}$$

In the above equation, n is a "forgetting factor", n may vary between 0 and 1, and its value dictates how fast old measurements are forgotten by the model. For values of n close to 1, the model adapts more quickly to recent measurements. For values of n close to 0, the model adapts more slowly to recent measurements. The value of n may depend on the elapsed time since the sensor was implanted. The calculation may be recursive or non-recursive. While a fixed forgetting factor n may be used, in some embodiments the forgetting factor n may be adaptive in real-time based on the calculated drift rate. For example, adaptive adjustment of the forgetting factor n may be based on a metric indicative of how much of the total error in the system is due to drift. If most of the error is due to drift, then our drift estimate is may be too aggressive or not aggressive enough, so the forgetting factor in the adaptive adjust (e.g. $\text{Drift}_{estimate}$) should be closer to 1, resulting in quicker adjustment of the time series. If the most of the error is random then there is no need to update $\text{Drift}_{estimate}$ so the forgetting factor in the adaptive adjust (e.g. $\text{Drift}_{estimate}$) should be closer to 0. One metric useful for determining much of the total error in the system is due to drift is to determine a ratio of the relative error (e.g., smoothed error) at calibration to the absolute error at calibration, and use an absolute value of that ratio for n (or to determine n). In the initial calculation of the ratio RelativeError and AbsoluteError may use seed values, after which the previous estimate may be used in the following equations: $\text{RelativeError}_N = \text{Beta}^*\text{ErrorAtCal} + (1-\text{Beta})^*\text{RelativeError}_{N-1}$ and $\text{AbsoluteError}_N = \text{Beta}^* |\text{ErrorAtCal}| + (1-\text{Beta})^*\text{AbsoluteError}_{N-1}$, where Beta is a forgetting factor for these equations.

In certain of the present embodiments, drift rate is calculated only after a minimum amount of time has passed since the sensor was initialized. As discussed above, it is known that new sensors output unpredictable readings in the early stages after implantation. This behavior is due to the fact that penetration of fluid and tissue to the sensor does not happen immediately upon implantation. Rather, the sensor "settles" with its surroundings. Readings taken during this settling period may be subject to random error, and may therefore be unreliable. These readings are preferably disregarded because drift error is preferably greater than random error in order to accurately determine a drift compensation function to apply to sensor data. In one example, the minimum amount of time that preferably passes after sensor initialization is three hours. However, the minimum amount of time may be any amount of time, including less than three hours and more than three hours.

In some embodiments, changes in impedance of the sensor, or any measurable response to a stimulus signal, may be used to track changes in sensitivity of the sensor. A relationship between sensitivity and impedance has been observed in some analyte sensors. Although not wishing to be bound by theory, embodiments of analyte sensors are believed to have a relationship between an impedance of a sensor's membrane and the diffusivity of the membrane. For example, a change in impedance of an analyte sensor can indicate a proportional change in diffusivity of the analyte sensor's membrane. Further, an increase in diffusivity can yield an increased transport of the analyte being measured (e.g., glucose) through the membrane, resulting in an increased sensor output current. That is, a change in diffusivity can result in a proportional change in sensor sensitivity. Other factors may also contribute to changes in sensitivity apart from just changes in diffusivity of the sensor membrane, depending upon the characteristics of sensor and the environment in which the sensor is used.

A relationship between sensitivity and impedance can be used to estimate a sensor sensitivity value and/or correct for sensitivity changes of the sensor over time, resulting in increased accuracy, a reduction in required calibrations or both. In addition to detection of sensitivity, some embodiments can detect other characteristics of an analyte sensor system based on measurements of electrical impedance over one or more frequencies. These characteristics include, but are not limited to, temperature, moisture ingress into sensor electronics components and sensor membrane damage.

In some embodiments, a relationship between a sensor's impedance and the sensor's sensitivity can be used to calculate and compensate for sensitivity changes of an analyte sensor. For example, a change in impedance of an analyte sensor can correspond to a proportional change in sensitivity of the sensor. In addition, an absolute value of an impedance of an analyte sensor can correspond to an absolute value of the analyte sensor's sensitivity and the corresponding sensitivity value can be determined based on a predetermined relationship determined from prior studies of similar sensors. Sensor data can then be compensated for changes in sensitivity based on an impedance to sensitivity relationship.

Figure 16:
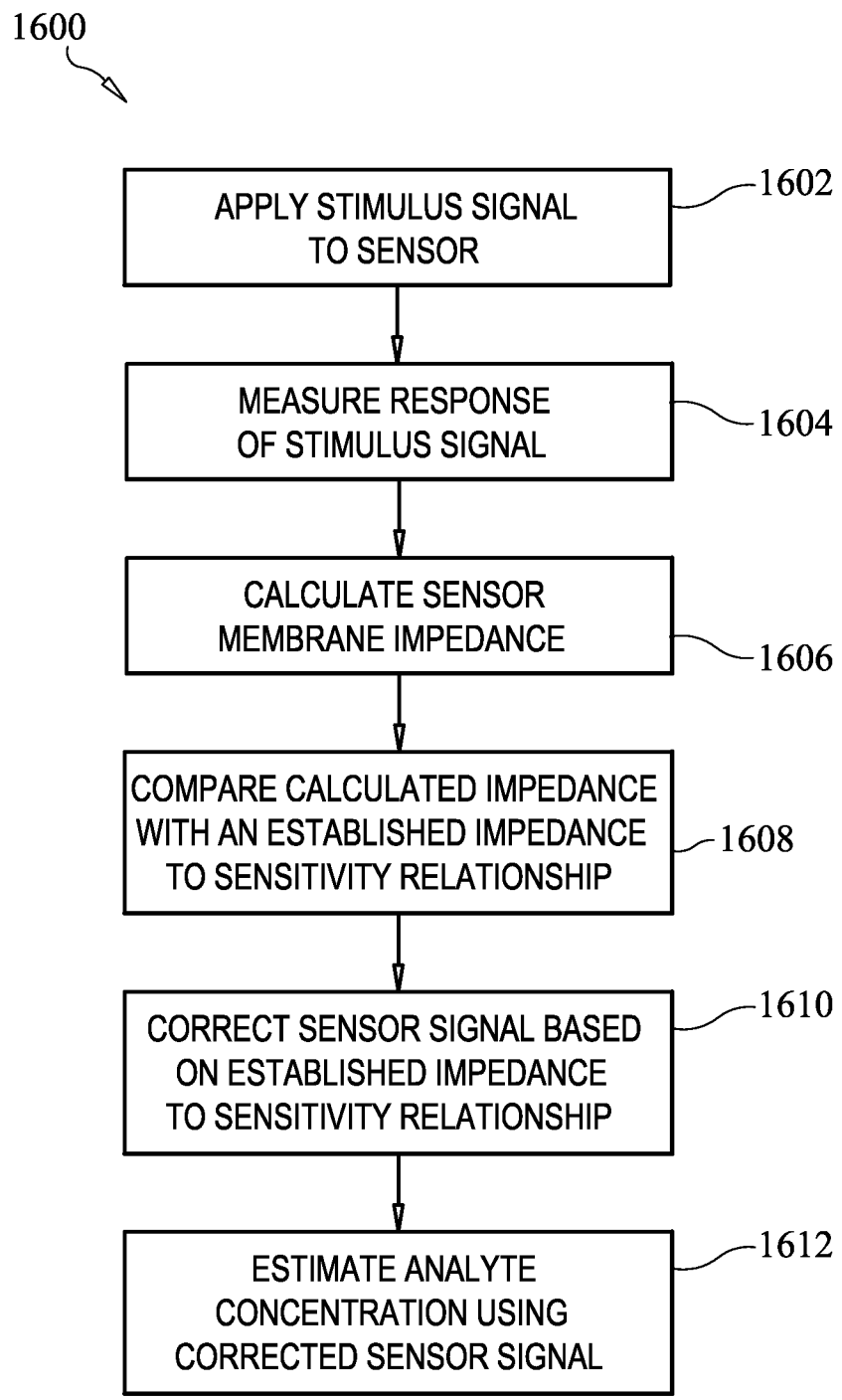
FIG. 16 is a flowchart illustrating a process for compensating sensor data for changes in sensitivity, in accordance with the present embodiments.

FIG. 16 is a flowchart illustrating a process 1600 for compensating sensor data for changes in sensitivity in accordance with the present embodiments. At step 1602, a stimulus signal is applied to the sensor that can be used to determine an impedance of the sensor's membrane. The stimulus may be, for example, a signal having a given frequency, as discussed with respect to FIG. 10, or a voltage step, as discussed with respect to FIGS. 11-13. A response to the input signal is then measured at step 1604 and an impedance of the sensor's membrane is calculated based on the response at step 1606. Next, at step 1608, the calculated impedance is compared to an established impedance-to-sensor sensitivity relationship. The established relationship can be determined from prior studies of analyte sensors that exhibit similar sensitivity-to-impedance relationships as the analyte sensor currently under test, for example, sensors that were made in substantially the same way under substantially the same conditions as the sensor currently under test. At step 1610, a sensor signal (e.g., in units of electrical current or counts) of the sensor currently under test is corrected using the impedance to sensitivity relationship. An estimated analyte concentration value or values is then calculated based on the corrected sensor signal at step 1612 using, for example, a conversion function. The estimated analyte concentration values can then be used for further processing and/or outputting, such as displaying information representative of the estimated values on a user device and/or outputting the information to an external device.

It should be understood that the process 1600 is only one example of using an impedance of a sensor to compensate for changes in sensor sensitivity, and that various modifications can be made to the process 1600 that fall within the scope of the present embodiments. For example, an established impedance-to-sensitivity relationship can be used to determine a sensitivity value of the sensor under test, and the sensitivity value can then be used to modify or form a conversion function used to convert a sensor signal of the sensor under test into one or more estimated glucose concentration values. In addition, instead of calculating an impedance based on the stimulus signal response, one or more properties of the stimulus signal response (e.g., peak current value, counts, etc.) can be directly correlated to a sensitivity based on a predetermined relationship between the stimulus signal property and the sensitivity.

Some embodiments use one or more impedance values of the sensor to form, modify or select a sensitivity profile, also referred to as a sensitivity drift curve, of an analyte sensor. A sensor can have a sensitivity profile that indicates the sensor's change in sensitivity over time. Although sensors made in substantially the same way under substantially the same conditions can exhibit similar sensitivity profiles, the profiles can still vary. For example, the environment in which a particular sensor is used can cause the sensor's sensitivity profile to differ from other, similar sensors. Accordingly, some embodiments can, for example, select a sensitivity profile out of a plurality of predetermined sensitivity profiles based on a correlation of the calculated one or more impedance values to the selected sensitivity profile. Further, some embodiments modify a sensor sensitivity profile already associated with the analyte sensor under test to more closely predict the sensor's sensitivity profile, where the modification is based on the one or more impedance values.

Figure 17:
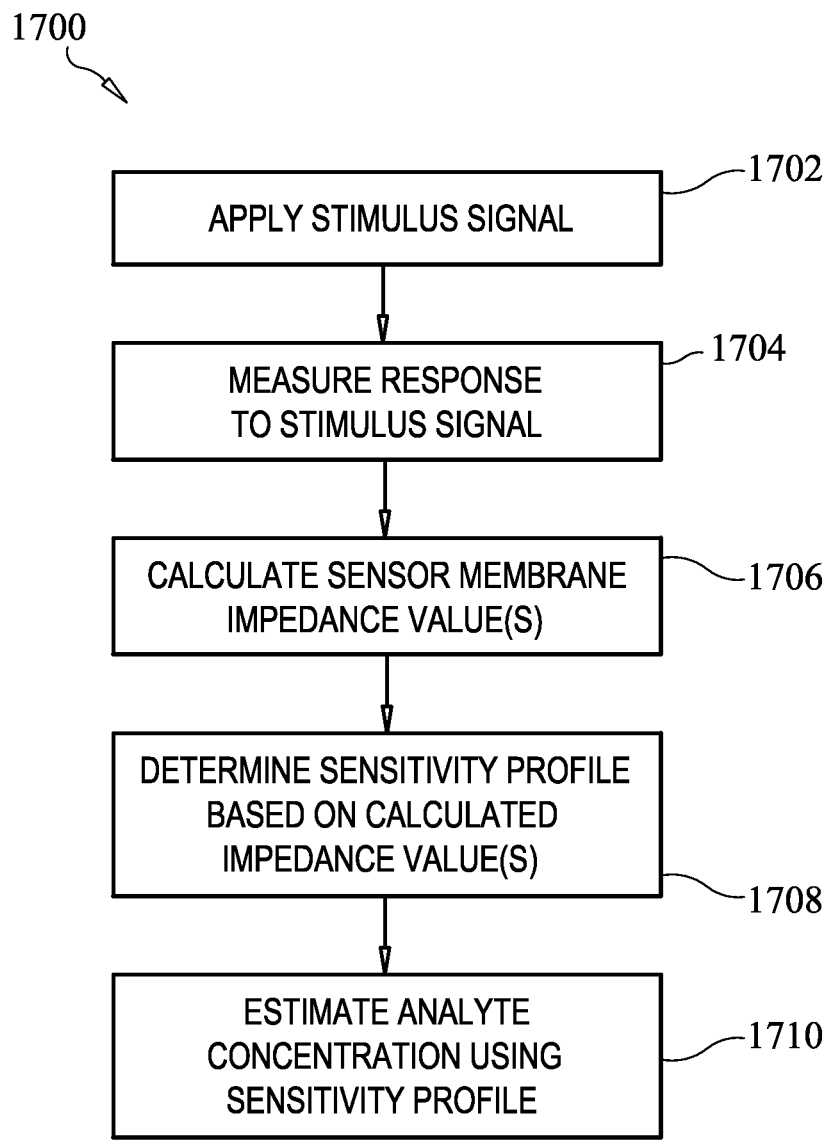
FIG. 17 is a flowchart illustrating a process for determining a predicted sensitivity profile using one or more sensor membrane impedance values, in accordance with the present embodiments.

FIG. 17 is a flowchart illustrating a process 1700 for determining a predicted sensitivity profile using one or more sensor membrane impedance values, in accordance with the present embodiments. At step 1702, a stimulus signal is applied to an analyte sensor under test and a response is measured at step 1704. Next, one or more sensor membrane impedance values are calculated based on the response at step 1706. Various techniques for calculating sensor membrane impedance values based on the response that can be used in process 1700 are described elsewhere herein, such as one or more of the techniques discussed with reference to FIGS. 10-13. A sensitivity profile is then determined based on the one or more calculated impedance values in step 1708. Process 1700 then calculates (which can include retrospectively correcting and/or prospectively calculating) estimated analyte concentration values using the determined sensitivity profile. The estimated analyte concentration values can then be used for further processing and outputting, such as displaying information representative of the estimated values on a user device and/or outputting the information to an external computing device.

Further to step 1708, various techniques can be used to determine the sensitivity profile. One technique compares the one or more calculated impedance values to a plurality of different predicted sensitivity profiles and selects a predicted sensitivity profile that best fits the one or more calculated impedance values. The plurality of different predicted sensitivity profiles can be stored in memory of the sensor electronics, for example. Another technique includes using an estimative algorithm to predict or determine a sensitivity profile based on the one or more calculated impedance values. A further technique includes determining a sensitivity profile by modifying a sensitivity profile associated with the sensor under test. Modifying the sensitivity profile can include using an estimative algorithm to modify the sensitivity profile to more closely track the sensitivity profile of the sensor under test based on the one or more calculated impedance values.

Some embodiments compare one or more impedance values of an analyte sensor under test to a predetermined or predicted sensitivity profile associated with the sensor to determine if the sensor is functioning properly. A sensor can be predicted to have a particular sensitivity profile based on, for example, a study of sensitivity changes over time of sensors made in substantially the same way and used under substantially the same conditions. However, it can be determined that a sensor is functioning improperly—due to, for example, improper sensor insertion, damage to the sensor during shipping, manufacturing defects and the like—if the sensor is found not to be sufficiently tracking its predicted sensitivity profile based on sensitivities derived from impedance measurements of the sensor. Put another way, it can be determined that a sensor is not functioning properly if one or more impedance values of a sensor's membrane do not sufficiently correspond to a predicted sensitivity profile of the sensor, for example, because the impedance of a sensor membrane can indicate a sensitivity of the sensor.

Figure 18:
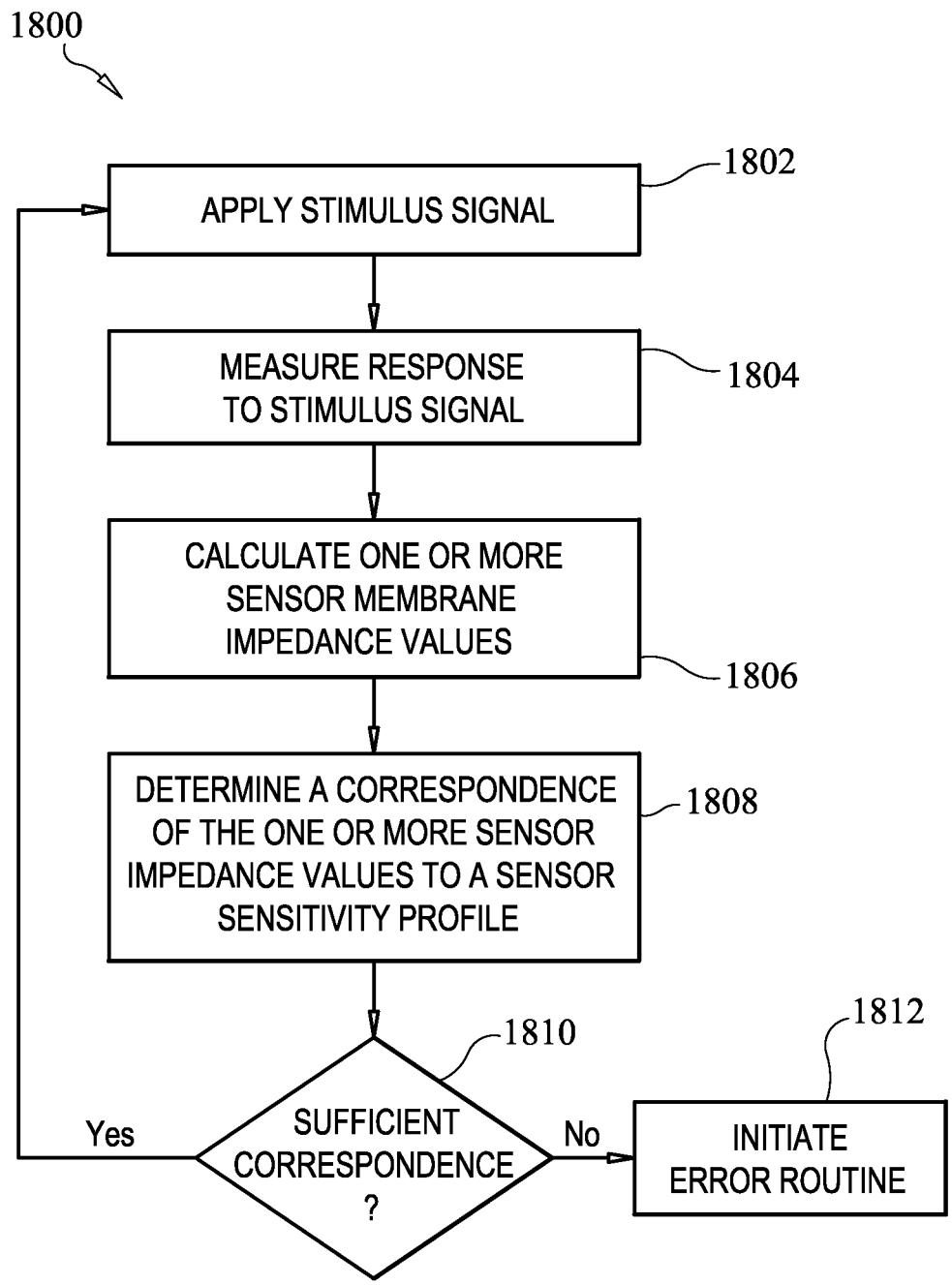
FIG. 18 is a flowchart illustrating a process for determining whether an analyte sensor under test is functioning properly based on a predicted sensitivity profile and one or more impedance measurements, in accordance with the present embodiments.

FIG. 18 is a flowchart illustrating a process 1800 for determining whether an analyte sensor under test is functioning properly based on a predicted sensitivity profile (curve) and one or more impedance measurements, in accordance with the present embodiments. At step 1802, a stimulus signal is applied to an analyte sensor under test and a response is measured at step 1804. Next, one or more sensor membrane impedance values are calculated based on the signal response at step 1806. Various stimulus signals and techniques for calculating sensor membrane impedance values based on the signal response that can be used in the process 1800 are described elsewhere herein, such as any one of the techniques discussed with reference to FIGS. 10-13. The process 1800 then determines a correspondence of the one or more calculated impedance values to a sensitivity profile in step 1808. Next, in decision step 1810, the process 1800 queries whether the one or more calculated impedance values sufficiently correspond to the predicted sensitivity profile. If it is determined that the one or more calculated impedance values sufficiently correspond to the predicted sensitivity profile, then the process 1800 confirms proper operation of the analyte sensor under test. If confirmed to be proper in step 1810, the process 1800 may then be repeated after a predetermined time delay ranging from about 1 minute to 1 day, for example about 10 minutes, 1 hour, 12 hours, or 1 day. However, the process 1800 initiates an error routine 1812 if it is determined that the one or more calculated impedance values do not sufficiently correspond to the predicted sensitivity profile. Error routine 1812 can include triggering an audible alarm, displaying an error message on a user display, discontinuing display of sensor data on a user display, sending a message to a remote communication device over a communication network, such as a mobile phone over a cellular network or remote computer over the internet, and the like. The error routine can also include modifying the predicted sensitivity profile—based on the one or more impedance measurements, for example—or selecting a new predicted sensitivity profile based on the one or more impedance measurements. The modified predicted sensitivity profile or new predicted sensitivity profile can be a sensitivity profile that more closely corresponds to changes in sensitivity of the sensor under test based on the one or more impedance measurements as compared to the unmodified or previously used predicted sensitivity profile.

Further to step 1808 of the process 1800, various statistical analysis techniques can be used to determine a correspondence of the one or more impedance values to the predicted sensitivity profile. For example, correspondence can be determined based on whether a sensitivity value derived from the calculated impedance value (e.g., derived from a predetermined relationship of impedance and sensitivity) differs by no less than a predetermined threshold amount from a predicted sensitivity value as determined from the predicted sensitivity profile. The predetermined threshold amount can be in terms of an absolute value or a percentage. As another example, correspondence can be determined based on a data association function. The term "data association function," as used herein, is used in its ordinary sense, including, without limitation, a statistical analysis of data and particularly its correlation to, or deviation from, a particular curve. A data association function can be used to show data association. For example, sensor sensitivity data derived from impedance measurements described herein may be analyzed mathematically to determine its correlation to, or deviation from, a curve (e.g., line or set of lines) that defines a sensor sensitivity profile. This correlation or deviation is the data association. A data association function can also be used to determine data association. Examples of data association functions include, but are not limited to, linear regression, non-linear mapping/regression, rank (e.g., non-parametric) correlation, least mean square fit, mean absolute deviation (MAD), mean absolute relative difference. In one such example, the correlation coefficient of linear regression is indicative of the amount of data association of sensitivity data derived from impedance measurements from a sensitivity profile, and thus the quality of the data and/or sensitivity profile. Of course, other statistical analysis methods that determine a correlation of one or more points to a curve can be used in the process 1800 in addition to those described herein.

The processes 1700, 1800 can use one or more impedance values. When more than one impedance value is used, each impedance value can be time-spaced from the other impedance value(s). In other words, one impedance value can be taken at a first point in time $t_1$ (indicative of a sensor impedance at time $t_1$), a second impedance value can be taken at a second, later point in time $t_2$ (indicative of a sensor impedance at time $t_2$), and third impedance value taken at a third, even later point in time $t_3$ (indicative of a sensor impedance at time $t_3$), and so on. Further, the time between $t_1$ and $t_2$ can be a first amount of time and the time between $t_2$ and $t_3$ can be a second amount of time that is either the same as or different from the first amount of time. The time-spaced impedance values can then be used separately or combined using a statistical algorithm (e.g., calculating an average or median value of the time-spaced values). The separate values or combined value can then be used to determine a sensitivity value and/or sensitivity profile in step 1708 of the process 1700 or determine a correspondence with a sensitivity profile in step 1808 of the process 1800, for example. Additionally or alternatively, one or more of the impedance values can be taken at substantially the same time, but each derived using a different measurement technique, such as any of the measurement techniques described herein. For example, a first impedance can be calculated using a step voltage technique as described in the process of FIG. 12, and a second impedance can be calculated using a sine wave overlay technique as described in the process of FIG. 10. The impedance values derived from different measurement techniques can then be applied to a statistical algorithm (e.g., calculating an average or median value) to determine a processed impedance value. The processed impedance value can then be used to determine a sensitivity value and/or sensitivity profile in step 1708 of the process 1700 or determine a correspondence with a sensitivity profile in step 1808 of the process 1800, for example.

Temperature

Some embodiments can use signal processing techniques to determine a temperature of the sensor. For example, a stimulus signal can be applied to a sensor and a signal response measured and, based on the signal response, a temperature of the sensor can be derived.

An impedance of a sensor membrane, as determined using one of the techniques described with reference to FIGS. 10-13, for example, can be used to estimate a temperature of the sensor in accordance with the present embodiments. Although not wishing to be bound by theory, it is believed that sensitivity of a sensor is affected by temperature, where a higher temperature can result in a higher sensitivity and a lower temperature can result in a lower sensitivity. Similarly, because an impedance of a sensor membrane can have a direct relationship to the sensor's sensitivity, it is believed that a higher temperature can result in lower impedance and a lower temperature can result in a higher impedance. That is, sensitivity and impedance can have a direct relationship to the sensor's temperature. Accordingly, using a known relationship between impedance and temperature—based on previously conducted studies of substantially similar sensors, for example—one can estimate a sensor's temperature based on a sensor impedance measurement.

In some embodiments, a temperature sensor may be provided on or in the sensor 102 at a working electrode of the sensor so that the temperature sensor is placed subcutaneously in a host along with the sensor 102. Other implementations may use electrochemistry techniques, such as Electrochemical Impedance Spectroscopy (EIS), to measure the temperature at the working electrode.

In some embodiments, a temperature sensor may be placed in the sensor assembly 100 at a location that is on or near the host's skin surface. The temperature sensor may be integral with the sensor assembly 100, such that it is disposed of, along with the sensor 102 and the sensor assembly 100, at the end of the life of the sensor 102. The temperature sensor may be in direct contact with the skin, or be coated or potted in a material that has good thermal conductivity. The material may include an adhesive pad. In addition, the temperature sensor (or thermal conductive material) may be surrounded with a thermally insulating material to prevent external temperature changes from impacting the temperature sensing. The temperature sensor may be designed into the sensor assembly 100 to reduce or eliminate any air gap between the skin and the thermal conductive material or temperature sensor.

In some embodiments, the temperature sensor is an integral component of the sensor electronics 104. To measure as close as possible to the temperature at the working electrode, several implementations may be used, as discussed below.

In some embodiments, a temperature sensor may be provided on an underside of an adhesive pad or base of the sensor assembly 100 in the form of a screen printed thick film material that changes resistance as a function of temperature. For example, the material may be printed in the form of a meandering path. By measuring the electric resistance of this meander, the skin temperature may be estimated. An example of suitable material that has a high temperature-dependent resistance is semiconductors like doped silicon. A screen printable ink based on small particles (e.g., 1-20 μm) may be formulated.

Figure 19:
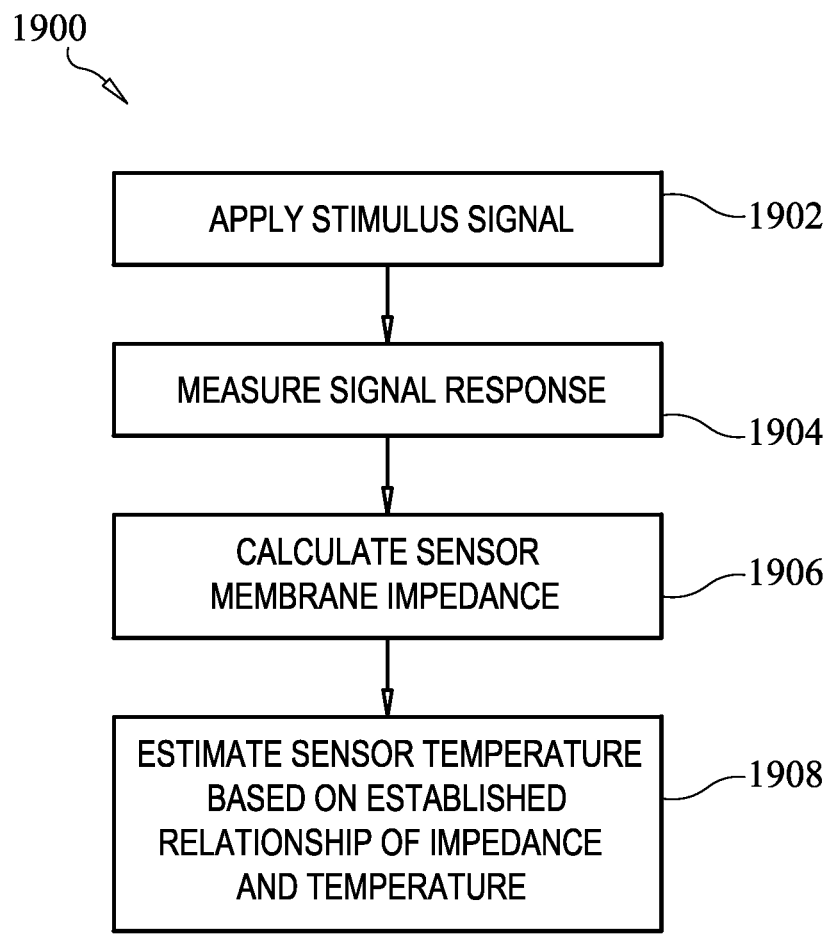
FIG. 19 is a flowchart illustrating a process for determining a sensor temperature, in accordance with the present embodiments.

FIG. 19 is a flowchart illustrating a process 1900 for determining a sensor temperature, in accordance with the present embodiments. At step 1902, a stimulus signal is applied to an analyte sensor under test, and a response is measured and recorded at step 1904. Impedance is calculated based on the signal response at step 1906. The impedance can be calculated using, for example, any of the techniques described herein such as those described with reference to FIGS. 10-13. A temperature of the sensor is then estimated based on a predetermined relationship between impedance and temperature at step 1908. The temperature can then be used to estimate analyte concentration values (e.g., glucose concentration) using sensor data. For example, the temperature can be used to compensate for temperature effects on sensor sensitivity and, based on the sensitivity compensation, more accurate analyte concentration values can be estimated.

A relationship between sensor sensitivity and different temperatures can be mathematically modeled (e.g., by fitting a mathematical curve to data using one of the modeling techniques used herein), and the mathematical model can then be used to compensate for temperature effects on the sensor sensitivity. That is, a sensitivity of a sensor (which is affected by the sensor's temperature) can be determined based on associating a measured impedance of the sensor to the mathematical curve. The predetermined relationship between impedance and temperature can be determined by studying impedances of similar sensors over a range of temperatures. Sensor data can then be converted to estimated analyte concentration values based on the determined sensor sensitivity.

As a non-limiting example, some embodiments of analyte sensors can have an essentially linear relationship of impedance to temperature after a sensor run-in period. The slope of the linear relationship can be established by studying sensors made in substantially the same way as the sensor under test over a range of temperatures. Thus, a sensor temperature can be estimated by measuring an impedance value of the sensor's membrane and applying the impedance value to the established linear relationship.

Some embodiments can compare a first sensor temperature, where the first temperature is derived from an impedance measurement of an analyte sensor, with a second sensor temperature, where the second sensor temperature can be derived independent from the impedance measurement. The second estimated temperature can be measured using a thermistor, for example. The thermistor can be configured to measure an in vivo or ex vivo temperature, and can be located on the analyte sensor or separate from the analyte sensor. As non-limiting examples, the thermistor can be integral with the analyte sensor, positioned on the surface of the skin of a host adjacent to an insertion site in which the analyte sensor is implanted, positioned on the skin of the host at a location away from the insertion site or spaced apart from the host entirely, such as on a handheld device carried by the host. Factors contributing to a change in sensor sensitivity or a change in other sensor properties can then be determined or confirmed based, at least in part, on the comparison of the first and second temperatures.

In certain embodiments, the system may prompt the user to input one or more reference BG values in response to a measured sensitivity change. For example, where a measured sensitivity change is high, such as at or above a threshold value, the system may prompt the user for one or more BG values. If the BG values do not correlate with the measured sensitivity change, the sensor may be malfunctioning and may need to be replaced.

In some embodiments, host-specific measured values can be stored and used later for various purposes. For example, these values can be used as seed values, for validating later-taken measurements, for personalized drift compensation, etc. Example values that can be stored and used later include sensitivity (m), baseline (b), change in sensitivity ($\Delta$m), change in baseline ($\Delta$b), sensitivity at implant ($m_{implant}$) baseline at implant ($b_{implant}$), sensitivity at end-of-life ($m_{end\text{-}of\text{-}life}$), baseline at end-of-life ($b_{end\text{-}of\text{-}life}$), drift profile (e.g., sensitivity drift curve and/or baseline drift curve), etc.

Figure 20:
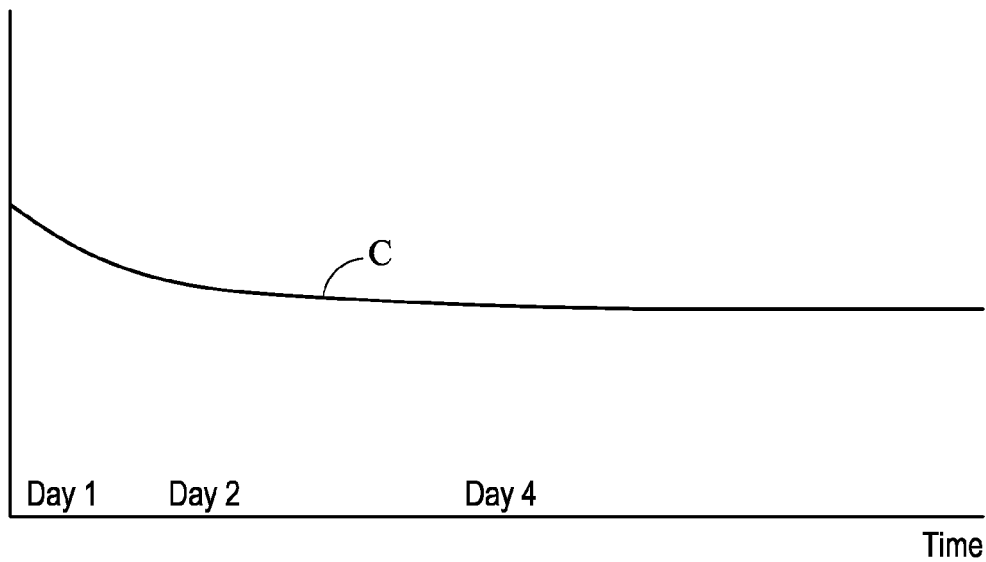
FIG. 20 is a graph illustrating a drift compensation function for a signal from a continuous analyte sensor.
Figure 21:
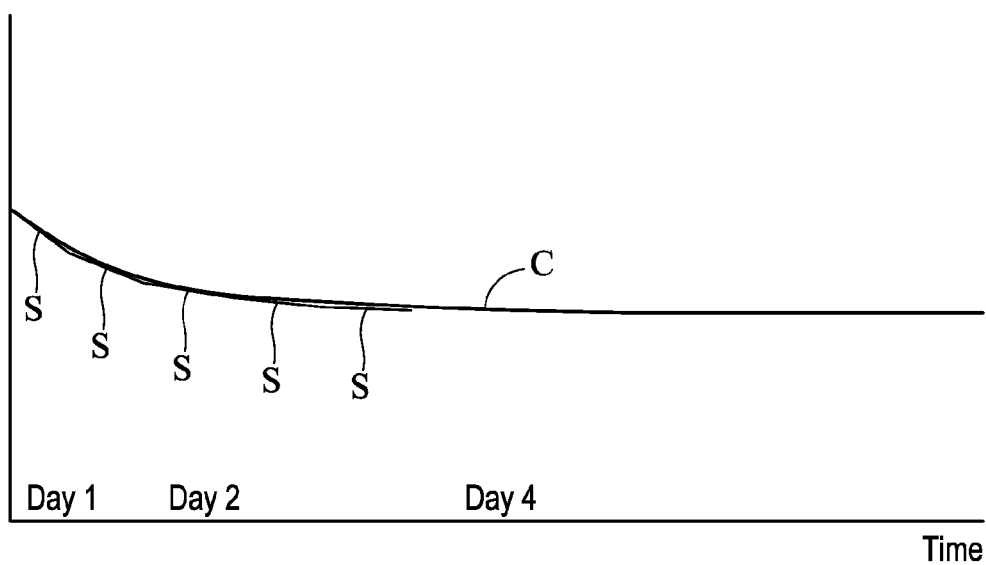
FIG. 21 is a graph illustrating a linear piece-wise function for applying the drift compensation function of FIG. 20 to the signal from the continuous analyte sensor.

Determining a Drift Compensation Function (Sensitivity or Baseline Shift) to be Applied In the present embodiments, a variety of different drift compensation functions may be applied after the change in sensitivity and/or baseline has been measured. One example of a drift compensation function is a stepwise function, which may be a linear piece-wise function. The linear piece-wise function is described with reference to FIGS. 20 and 21. FIG. 20 represents an ideal compensation curve C to be applied to a given drift curve. It is ideal in the sense that it is a mirror image of the drift curve, so that if the compensation curve and the drift curve were superimposed they would resolve to a straight, horizontal line, as in FIG. 6. A variety of methodologies may be employed, as is appreciated by a skilled artisan, to obtain drift curves and compensation functions. In one example, data from subjects without diabetes was assumed to have an average constant at approximately 100 mg/dL, the raw sensor signal was plotted as a function of time, and the function that best represented the data was determined using commercially-available software (e.g., TableCurve), after which the mathematical inverse was applied to the raw sensor signal, thereby de-convolving (removing) the drift. In another example, data from subjects with diabetes was filtered to isolate a band of the raw signal associated with a narrow range of glucose (e.g., 80-120 mg/dL), after which the methodology from the previous example was applied.

FIG. 20 illustrates a smooth curve C in the region spanning the first day or two after the sensor is implanted. This is the curve that represents how to compensate for sensor drift at periodic intervals, such as every one, two, five, ten or fifteen minutes. But, for practical reasons, the sensor is recalibrated at longer intervals, such as, for example, every six hours. Thus, with reference to FIG. 21, the linear piece-wise function breaks the ideal curve C into a plurality of discrete line segments S, where a length of each segment S corresponds to the interval between recalibrations. The slope at the center of the curve C within each segment S is used as the drift compensation function for that interval. At the end of each interval, another recalibration occurs and the applied drift compensation function is adjusted as necessary.

In some embodiments, a family of transform functions may be applied to the sensor data, where the family of transform functions represents a family of curves or compensation functions spanning a range of acceptability. Then, one of the transform functions may be selected from the family. For example, the transform function that causes the conversion function to be most linear or most accurate with respect to observed drift may be selected, similar to the example shown in FIG. 6, wherein the selected compensation function is one that effectively nulls the sensors drift. In another example, multiple compensation functions are applied to the calibrations set and the function that results in the best model between reference glucose value and drift-compensated sensor value is selected. For example, it is believed that changes in impedance track changes in sensitivity. Thus, changes in impedance can be mapped on a curve, and that curve may line up most closely with one of the transform functions. The more data gathered, the more it informs which transform function to select. Further, with hindsight information, it may be determined that a current conversion function is not the best conversion function, so another conversion function in the set may be selected instead. The family of transform functions may, for example, include a "do nothing" family member that may be applied if it is determined that the sensor has been restarted.

In some embodiments, an applied drift compensation function comprises a mathematical inverse of the equation that defines the curve traced by the drift. For example, experimental results have shown that for the subject population using certain example continuous glucose sensors, the drift follows a simple second-order polynomial (quadratic) equation of the form $$y = a + bx + cx^2.$$

Thus, a simple transform function for the above drift equation is defined as $$T = \frac{1}{y} = \frac{1}{a + bx + cx^2},$$

which is the mathematical inverse of the drift equation. Application of the mathematical inverse of the drift equation removes the time-dependent drift, or upward trend, in the data, because the curves defined by the drift equation and the transform function, when superimposed, resolve to a straight horizontal line.

In some embodiments, an applied drift compensation function comprises an extended Kalman filter. The Kalman filter is an algorithm that yields an optimized estimate of a system's state. The algorithm works recursively in real time on streams of noisy input observational data, such as sensor measurements, and filters out errors using a least-squares curve-fit optimized with a mathematical prediction of the future state generated through a modeling of the system's physical characteristics. The model estimate is compared to the observation and this difference is scaled by a factor known as the Kalman gain, which is then fed back as an input into the model for the purpose of improving subsequent predictions. The gain can be "tuned" for improved performance. With a high gain, the filter follows the observations more closely. With a low gain, the filter follows the model predictions more closely. This method produces estimates that tend to be closer to the true unknown values than those that would be based on a single measurement alone or the model predictions alone.

With the Kalman filter, sensors provide measurements as inputs to the system. But such measurements are intermittent, sometimes with significant intervals between measurements. Also, the measurements may be corrupted with a certain amount of error, including noise. The Kalman filter algorithm is an optimized method for determining the best estimation of the system's state. The basic concept is similar to simple mathematical curve-fitting of data points using a least-squares approximation (where the deviation is squared so that negative errors will not cancel out positive ones) and enables predictions of the state into future time steps. The most basic concepts of the filter are related to interpolation and extrapolation, where data estimates are filled in between given points and the latter involves data estimates being extended beyond the given set (as with future estimates). In each time step, the Kalman filter produces estimates of the true unknown values, along with their uncertainties. Once the outcome of the next measurement is observed, these estimates are updated using a weighted average, with more weight being given to estimates with lower uncertainty.

The extended Kalman filter is the nonlinear version of the Kalman filter which linearizes about an estimate of the current mean and covariance. In the extended Kalman filter, the state transition and observation models need not be linear functions of the state but may instead be differentiable functions:

$$x_k = f(x_{k-1}, u_{k-1}) + w_{k-1}$$

$$z_k = h(x_k) + v_k$$

Where $w_k$ and $v_k$ are the process and observation noises which are both assumed to be zero mean multivariate Gaussian noises with covariance $Q_k$ and $R_k$ respectively.

The function $f$ can be used to compute the predicted state from the previous estimate and similarly the function h can be used to compute the predicted measurement from the predicted state. However, $f$ and h cannot be applied to the covariance directly. Instead a matrix of partial derivatives (the Jacobian) is computed. At each timestep the Jacobian is evaluated with current predicted states. These matrices can be used in the Kalman filter equations. This process essentially linearizes the non-linear function around the current estimate.

Extended Kalman filters have been proposed for continuous glucose monitoring. One difference in the present extended Kalman filter model, described below, is the sensitivity drift model. This model takes into account the decaying exponential increase in sensitivity that has been observed in experimental data. Using the extended Kalman filter model, sensor sensitivity is continuously updated by addition with a drift parameter, where the drift parameter is modeled as an exponentially correlated random variable. The drift parameter could also be modeled as a random ramp plus a random constant plus a random walk. For computational efficiency, EKF implementations, such as Fast Kalman Filtering or Variational Kalman Filtering, may be employed.

The equations below illustrate the present model.

Process

Random walk of rate of change (slope) of IG, where "ω1" is unknown, estimated during burn-in.

$$IG(k+1) = IG(k) + \text{slope}(k) + \begin{bmatrix} 1 & 0 \\ 0 & 1 \end{bmatrix} \begin{bmatrix} 0 \\ \omega_1 \end{bmatrix}$$

Sensitivity

IG is interstitial glucose, m is sensitivity, α is sensitivity drift, $\omega_\alpha$ is random noise affecting sensitivity drift (estimated), exponentially correlated random drift model (initialization and multiplier is estimated from group drift model).

$$m(k+1) = m(k) + \alpha(k)$$

$$\alpha(k+1) = 0.998\alpha(k) + \omega_\alpha$$

Baseline b is baseline, $\omega_\beta$ is random noise affecting baseline (estimated).

$$b(k+1) = b(k) + \omega_\beta$$

Measurements

SMBG: φ(k) is flag set to 1 when SMBG collected, $v_1$ can be guessed. Note this version is ignoring IG-BG kinetics $$SMBG = \phi(k)IG(k) + v_1(k)$$

Sensor Counts (SC): $v_2$ is measurement noise, ~ is not or inverse. Performed whenever SMBG is not collected $$SC = \sim\phi(k)[m(k)IG(k) + b(k) + v_2(k)]$$

Setup

Parameter vector x and measurement vector y:

$$\begin{bmatrix} IG \\ \text{slope} \\ m \\ b \\ \alpha \end{bmatrix} = \begin{bmatrix} x_1 \\ x_2 \\ x_3 \\ x_4 \\ x_5 \end{bmatrix} \quad \begin{bmatrix} SC \\ SMBG \\ m \\ b \end{bmatrix} = \begin{bmatrix} y_1 \\ y_2 \\ y_3 \\ y_4 \end{bmatrix}$$

State-Space Dynamic Model $$x(k+1) = f(x(k), \omega(k)) = \begin{matrix} x_1(k) + x_2(k) \\ x_2(k) + \omega_1(k) \\ x_3(k) + x_5(k) \\ x_4(k) + \omega_b(k) \\ 0.998 x_5(k) + \omega_\alpha(k) \end{matrix}$$

Measurement Model $$y(k) = h(x(k), v(k)) = \begin{bmatrix} \sim \phi(k)[x_1(k)x_3(k) + x_4(k) + v_1(k)] \\ \phi(k)[x_1(k) + v_2(k)] \\ \phi(k)[x_3(k) + v_3(k)] \\ \phi(k)[x_5(k) + v_5(k)] \end{bmatrix}$$

Note that these models are nonlinear. Therefore, the extended Kalman filter is required.

EKF Implementation

Estimation of state vector and covariance matrix:

$$\hat{x}(k+1|k) = f(\hat{x}(k|k), 0)$$

$$P(k+1|k) = A_k P(k|k) A_k^T + W_k Q_k W_k^T$$

Measurement Update $$K_k = P(k+1|k) H_k^T (H_k P(k+1|k) H_k^T + V_k R_k V_k^T)^{-1}$$

$$\hat{x}(k+1|k+1) = \hat{x}(k+1|k) + K_k(y(k+1) - h(\hat{x}(k+1|k), 0))$$

$$P(k+1|k+1) = (I - K_k H_k) P(k+1|k)$$

Where $A_k$ and $H_k$ are the Jacobian matrices of the partial derivatives of $f$ and h with respect to x.

$$A_k = \begin{bmatrix} 1 & 1 & 0 & 0 & 0 \\ 0 & 1 & 0 & 0 & 0 \\ 0 & 0 & 1 & 0 & 1 \\ 0 & 0 & 0 & 1 & 0 \\ 0 & 0 & 0 & 0 & 0.98 \end{bmatrix}$$

Note that $H_k$ changes every time (greater correction for higher IG and m).

$$W_k = I(5, 5)$$

$$V_k = I(3, 3) \text{ or } 1$$

$$Q(k) = \begin{bmatrix} 2{,}000 & & & & \\ & 4{,}000{,}000 & & & \\ & & 20 & & \\ & & & 20 & \\ & & & & 20 \end{bmatrix}$$

$$R(k) = \begin{bmatrix} 4 & & \\ & 16 & \\ & & 16 \end{bmatrix} \text{ or } 4$$

Prediction

Predict 5 minutes ahead to deal with filter time delay (possibly BG-IG kinetics):

$$x = A*x;$$

$$P = A*P*A' + Q;$$

In some embodiments, the calculated drift rate (e.g., measured or smoothed drift rate based on a BG value described in more detail elsewhere herein) at a specific point in time (e.g. t0) is used to continuously (e.g., iteratively) adjust the sensor data for drift after t0 until the next drift rate calculation. In these embodiments, the adjustment value applied to each sensor data value is based on the calculated drift rate and the elapsed time since the calibration was taken. For example, by determining the time (e.g., 5, 10, 15, 20, 25, 30 minutes and so on) since t0 and multiplying by the calculated drift rate (e.g., 0.5% per hour), the result is an adjustment value (or scaling factor) that is applied to adjust the sensor data (e.g., raw signal or EGV) at that time (e.g., 5, 10, 15, 20, 25, 30 minutes and so on). Accordingly, the further the current time is from t0, the more adjustment is applied. In some embodiments, the adjustment value may plateau (i.e., remain at the same adjustment value) at a fixed time point after t0 (e.g., 10 hours) until a new calibration occurs. In these embodiments, variables that may be adjusted within the drift compensation function include drift envelope drift rates (e.g. the max correction rate that can be applied in a given time window), start time of compensation (e.g. the time after sensor insertion that the drift compensation function starts), end time of the drift compensation function, start time of the different time windows in the drift envelope, length of time windows (steps in a stepwise function), or the like, which may be adaptive based on a seed value, a measured drift rate, reliability information, or the like.

In some embodiments, boundaries may be applied to the drift compensation function in order to ensure that the applied drift compensation function is appropriate for the measured drift rate. These boundaries may be based on a priori knowledge. For example, for a given drift rate, an applied compensation function may have a rate of compensation that falls within a certain range. If the rate of compensation is outside that range, an appropriate adjustment may be made. Further, the applied boundaries could be adaptive over time. For example, as the drift rate of the sensor decreases, confidence in the accuracy of data output from the sensor increases. Thus, narrower boundaries may be applied as confidence in the sensor increases.

In other embodiments, boundaries may be applied to detect errors in sensor readings and/or reference analyte readings. Where such errors are detected, the system may be configured to not report those values to the user. This aspect would have the advantageous effect of bolstering the user's confidence in the accuracy of the monitoring system, thereby making it more likely that the user would use the monitoring system. As discussed above, the applied boundaries could be adaptive over time.

In some embodiments, multiple drift compensation techniques may be applied in parallel. For example, a first drift estimate may be made based on impedance of the sensor, and a second drift estimate may be made based on a BG value. A predetermined correlation may then be required between the first and second drift estimates. If the predetermined correlation is not met, the two measurements may then be repeated as many times as necessary until the predetermined correlation is met.

In some embodiments, an appropriate drift compensation function may be inferred from an absolute sensitivity of the sensor. It has been observed that sensor sensitivity usually levels off at roughly the same place. Thus, a higher sensitivity at implant indicates that a more gradual sensitivity drift profile should be used and vice versa.

As discussed above, host-specific measured values can be stored and used later for various purposes. Another example of how these values can be used includes determining the drift profile/drift compensation function. Example values that can be stored and used later include sensitivity (m), baseline (b), change in sensitivity ($\Delta m$), change in baseline ($\Delta b$), sensitivity at implant ($m_{implant}$), baseline at implant ($b_{implant}$), sensitivity at end-of-life ($m_{end-of-life}$), baseline at end-of-life ($b_{end-of-life}$), drift profile, etc.

Applying Drift Compensation Function to Sensor Values Until Next Measurement of Sensitivity Change Once the appropriate drift compensation function to be applied is determined, it is applied to the sensor data. The drift compensation function may be applied to, for example, the raw sensor signal or converted (calibrated) signals. The drift compensation function may be applied pre-processing or post-processing. In pre-processing, the drift compensation function is applied to the sensor data in real time. In post-processing, the drift compensation function is applied to the sensor data retrospectively.

In some embodiments, the drift compensation function may be applied to all data output by the sensor. In other embodiments, the drift compensation function may not be applied to some of the data output by the sensor. For example, the drift compensation function may ignore outlying data points, or may be applied to every other data point, every third data point, etc. In still other embodiments, the drift compensation function may be applied at set time intervals, such as every two hours, every hour, every half-hour, every fifteen minutes, etc.

Certain embodiments may include an automatic stop function for the drift compensation function. For example, it has been observed that drift largely disappears after a certain amount of time has elapsed since implantation of the sensor. Thus, the system may be configured to stop applying drift compensation after the sensor has been implanted for a certain number of hours or days, such as three days for example. In an alternative embodiment, the system may be configured to stop applying drift compensation when the measured sensitivity change falls below a certain threshold. For example, the threshold may be less than a 5% change, less than a 4% change, less than a 3% change, less than a 2% change, less than a 1% change, etc.

Other Algorithmic Responses to Measured Drift Change

In addition to the above embodiments, a variety of other algorithmic responses may be applied to a measured drift change. For example, a weighting of matched data pairs may be dynamically adjusted in response to drift. When the drift rate is high, older matched data pairs may be given less weight. This technique focuses the applied drift compensation on more recent matched data pairs, which are closer in magnitude to the real-time drift rate. The resulting applied drift compensation thus more closely matches the real-time drift rate. As the rate of drift decreases, the weight given to older data pairs may rise. Additionally or alternatively, subsequent to the determination of the drift rate, sensor values of the matched data pairs may be retrospectively adjusted within each matched data pair by adjusting the sensor value according to the determined amount of drift at the time corresponding to the matching of the data pair. Advantageously, the retrospective adjustment of matched data pairs provides for drift-corrected sensor readings that are more consistent with the calibration model used for a stable sensor. For example, if the calibration model is a first-order polynomial then matched pairs (reference glucose and sensor counts) are expected to lie on a line. The presence of sensor drift degrades this relationship with a time-dependent error that, for example, can cause the oldest matched pairs to be below the best-fit line and the newest matched pairs to be above the line. When a useful drift correction is applied to the matched pairs it results an improved agreement between the matched pairs agreement and the model. This agreement may be quantified with standard regression metrics that assess fit quality such as correlation coefficient, sum of squared errors, or uncertainty of the resulting slope and baseline, which quantified agreement may be used in further processing of the sensor data. While many of the examples described here apply a correction to the glucose values based on the sensor signal these techniques can be applied to correct the reference values as a function of time to produce equivalent results.

In some embodiments, if a measured drift rate is greater than a threshold value, a calibration function may be restarted. For example, if the measured drift rate is greater than the high end of this range by a predetermined amount, or percentage, such as 1%, 2%, 3%, 4%, 5%, 10%, 15%, 20%, 30%, 40%, 50%, 60%, 70%, 80%, 90%, or 100%, it is likely to be erroneous, and the calibration function may be restarted.

In some embodiments, the conversion function may change over time as the drift rate changes. For example, the conversion function may consider all matched data pairs in a given window of time, where the length of that time may vary. During a period of severe drift, the window of time may be shorter, whereas when drift levels off the window of time may lengthen. Alternatively, the number of matched pairs in the calibration set may change over time. During a period of severe drift, fewer and more recent data pairs may be considered, whereas when drift levels off more data pairs may be considered.

In some embodiments, if the sensor is exhibiting characteristics, such as drift, that are extreme and not within expected boundaries based on a priori knowledge, a process may be restarted. For example, an applied compensation algorithm may be restarted, or the sensor may be restarted.

Methods and devices that are suitable for use in conjunction with aspects of the preferred embodiments are disclosed in U.S. Pat. Nos. 4,757,022; 4,994,167; 6,001,067; 6,558, 321; 6,702,857; 6,741,877; 6,862,465; 6,931,327; 7,074, 307; 7,081,195; 7,108,778; 7,110,803; 7,134,999; 7,136, 689; 7,192,450; 7,226,978; 7,276,029; 7,310,544; 7,364, 592; 7,366,556; 7,379,765; 7,424,318; 7,460,898; 7,467, 003; 7,471,972; 7,494,465; 7,497,827; 7,519,408; 7,583, 990; 7,591,801; 7,599,726; 7,613,491; 7,615,007; 7,632, 228; 7,637,868; 7,640,048; 7,651,596; 7,654,956; 7,657, 297; 7,711,402; 7,713,574; 7,715,893; 7,761,130; 7,771, 352; 7,774,145; 7,775,975; 7,778,680; 7,783,333; 7,792, 562; 7,797,028; 7,826,981; 7,828,728; 7,831,287; 7,835, 777; 7,857,760; 7,860,545; 7,875,293; 7,881,763; 7,885, 697; 7,896,809; 7,899,511; 7,901,354; 7,905,833; 7,914, 450; 7,917,186; 7,920,906; 7,925,321; 7,927,274; 7,933, 639; 7,935,057; 7,946,984; 7,949,381; 7,955,261; 7,959, 569; 7,970,448; 7,974,672; 7,976,492; 7,979,104; 7,986, 986; 7,998,071; 8,000,901; 8,005,524; 8,005,525; 8,010, 174; 8,027,708; 8,050,731; 8,052,601; 8,053,018; 8,060, 173; 8,060,174; 8,064,977; 8,073,519; 8,073,520; 8,118, 877; 8,128,562; 8,133,178; 8,150,488; 8,155,723; 8,160, 669; 8,160,671; 8,167,801; 8,170,803; 8,195,265; 8,206, 297; 8,216,139; 8,229,534; 8,229,535; 8,229,536; 8,231, 531; 8,233,958; 8,233,959; 8,249,684; 8,251,906; 8,255, 030; 8,255,032; 8,255,033; 8,257,259; 8,260,393; 8,265, 725; 8,275,437; 8,275,438; 8,277,713; 8,280,475; 8,282, 549; 8,282,550; 8,285,354; 8,287,453; 8,290,559; 8,290, 560; 8,290,561; 8,290,562; 8,292,810; 8,298,142; 8,311, 749; 8,313,434; 8,321,149; 8,332,008; 8,346,338; 8,364, 229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S.

Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013000536650A1; and U.S. Patent Publication No. 2013-0053666-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; U.S. application Ser. No. 13/784,523 filed on Mar. 4, 2013 and entitled "ANALYTE SENSOR WITH INCREASED REFERENCE CAPACITY"; U.S. application Ser. No. 13/789,371 filed on Mar. 7, 2013 and entitled "MULTIPLE ELECTRODE SYSTEM FOR A CONTINUOUS ANALYTE SENSOR, AND RELATED METHODS"; U.S. application Ser. No. 13/789,279 filed on Mar. 7, 2013 and entitled "USE OF SENSOR REDUNDANCY TO DETECT SENSOR FAILURES"; U.S. application Ser. No. 13/789,339 filed on Mar. 7, 2013 and entitled "DYNAMIC REPORT BUILDING"; U.S. application Ser. No. 13/789,341 filed on Mar. 7, 2013 and entitled "REPORTING MODULES"; and U.S. application Ser. No. 13/790,281 filed on Mar. 8, 2013 and entitled "SYSTEMS AND METHODS FOR MANAGING GLYCEMIC VARIABILITY".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of processing sensor data output by a continuous analyte sensor implanted within a body, comprising:
generating sensor data using a continuous analyte sensor implanted within a body of a host;
receiving and processing the sensor data output by the sensor using sensor electronics including a processor;
measuring a change in sensitivity or baseline of the sensor over a time interval;
determining a drift compensation function to be applied to a plurality of time-spaced data points output by the sensor over a next interval of time, wherein the drift compensation function is based at least in part on sensitivity information from a previous sensor session of the host; and
applying the drift compensation function continuously to the data points over the next interval of time.

2. The method of claim 1, wherein measuring the change in sensitivity or baseline of the sensor comprises comparing a measured sensitivity or baseline of the sensor to a predetermined sensitivity or baseline of the sensor.

3. The method of claim 2, wherein determining a drift compensation function to be applied is based, at least in part, on the predetermined sensitivity or baseline.

4. The method of claim 2, wherein a value of the predetermined sensitivity or baseline is encoded on sensor electronics.

5. The method of claim 1, further comprising comparing the measured change in sensitivity or baseline of the sensor to a priori knowledge regarding the change in sensitivity or baseline of the sensor over the time interval.

6. The method of claim 1, further comprising, based on the measured change in sensitivity or baseline of the sensor, determining whether the sensor has been previously used.

7. The method of claim 1, wherein measuring the change in sensitivity or baseline of the sensor occurs only after the sensor has been implanted within the body for at least a minimum duration.

8. The method of claim 1, further comprising prompting a user for a reference analyte value when the measured change in sensitivity or baseline of the sensor exceeds a criterion.

9. The method of claim 1, further comprising applying boundaries to the drift compensation function.

10. The method of claim 7, wherein the boundaries are based on a priori knowledge.

11. The method of claim 1, further comprising measuring an absolute sensitivity or baseline of the sensor at a time t, and wherein determining the drift compensation function to be applied to the plurality of time-spaced data points output by the sensor is based on the measured absolute sensitivity or baseline.

12. The method of claim 1, further comprising ceasing applying the drift compensation function continuously to the data points when the measured change in sensitivity or baseline of the sensor is below a threshold value.

13. The method of claim 1, further comprising ceasing applying the drift compensation function continuously to the data points after a predetermined amount of time has elapsed.

14. The method of claim 1, wherein the step of measuring a change in sensitivity or baseline of the sensor occurs over a first time interval, the step of determining a drift compensation function is based on the measured change in sensitivity or baseline of the sensor over the first time interval, and the step of applying the drift compensation function is to continuously adjust the sensor data output to compensate for changes in sensitivity or baseline of the sensor over a second time interval.

15. The method of claim 1, wherein measuring the change in sensitivity or baseline of the sensor comprises comparing a first measured sensitivity or baseline of the sensor to a second measured sensitivity or baseline of the sensor, wherein the first and second measured sensitivities or baselines of the sensor are taken at a beginning and an end, respectively, of the time interval.

16. The method of claim 15, wherein a value of the predetermined sensitivity or baseline of the sensor is assigned according to known characteristics of the body in which the sensor is implanted.

17. The method of claim 16, wherein the characteristics include at least one of age, body type, gender, diabetes type, diabetes duration, concomitant diseases and/or sensor location.

18. The method of claim 1, wherein measuring the change in sensitivity of the sensor over the time interval comprises calculating a drift rate of the sensor over the time interval.

19. The method of claim 18, wherein calculating the drift rate of the sensor comprises comparing measured analyte values to substantially time-corresponding reference analyte values.

20. The method of claim 19, wherein an expected drift rate of the sensor is calculated based on a weighted average of a current calculated drift rate and at least one previously measured drift rate.

21. The method of claim 1, wherein measuring the change in sensitivity or baseline of the sensor occurs only after the sensor has been implanted within the body for at least a minimum duration.

22. A system for processing data, the system comprising:
a continuous analyte sensor configured to be implanted within a body of a host; and
sensor electronics configured to receive and process sensor data output by the sensor, the sensor electronics including a processor configured to:
measure a change in sensitivity or baseline of the sensor over an interval of time;
determine a drift compensation function to be applied to a plurality of time-spaced data points output by the sensor over a next interval of time, wherein the drift compensation function is based at least in part on sensitivity information from a previous sensor session of the host; and
apply the drift compensation function continuously to the data points over the next interval of time.

23. The system of claim 22, wherein measuring the change in sensitivity or baseline of the sensor comprises comparing a first measured sensitivity or baseline of the sensor to a second measured sensitivity or baseline of the sensor, wherein the first and second measured sensitivities or baselines of the sensor are taken at a beginning and an end, respectively, of the time interval.

24. The system of claim 22, wherein the processor is further configured to compare a measured sensitivity or baseline of the sensor to a predetermined sensitivity or baseline of the sensor.

25. The system of claim 24, wherein determining a drift compensation function to be applied is based, at least in part, on the predetermined sensitivity or baseline.

26. The system of claim 24, wherein a value of the predetermined sensitivity or baseline is encoded on sensor electronics.

27. The system of claim 24, wherein a value of the predetermined sensitivity or baseline of the sensor is assigned according to known characteristics of the body in which the sensor is implanted.

28. The system of claim 27, wherein the characteristics include at least one of age, body type, gender, diabetes type, diabetes duration, concomitant diseases and/or sensor location.

29. The system of claim 22, wherein the processor is further configured to compare the measured change in sensitivity or baseline of the sensor to a priori knowledge regarding the change in sensitivity or baseline of the sensor over the time interval.

30. The system of claim 22, wherein measuring the change in sensitivity of the sensor over the time interval comprises calculating a drift rate of the sensor over the time interval.

31. The system of claim 30, wherein calculating the drift rate of the sensor comprises comparing measured analyte values to substantially time-corresponding reference analyte values.

32. The system of claim 30, wherein an expected drift rate of the sensor is calculated based on a weighted average of a current calculated drift rate and at least one previously measured drift rate.

33. The system of claim 22, wherein measuring the change in sensitivity or baseline of the sensor occurs only after the sensor has been implanted within the body for at least a minimum duration.

34. The system of claim 22, wherein the processor is further configured to prompt a user for a reference analyte value when the measured change in sensitivity or baseline of the sensor exceeds a criteria.

35. The system of claim 22, wherein the processor is further configured to store the change in sensitivity or baseline of the sensor for later use.

36. The system of claim 22, wherein the applied drift compensation function is a stepwise function.

37. The system of claim 22, wherein the applied drift compensation function functions to apply a mathematical inverse of a mathematical equation that describes the change in sensitivity or baseline of the sensor over the time interval.

38. The system of claim 22, wherein the processor is further configured to apply boundaries to the drift compensation function.

39. The system of claim 38, wherein the boundaries are based on a priori knowledge.

40. The system of claim 22, wherein the processor is further configured to measure an absolute sensitivity or baseline of the sensor at a time t, and wherein determining the drift compensation function to be applied to the plurality of time-spaced data points output by the sensor is based on the measured absolute sensitivity or baseline.

41. The system of claim 22, wherein the processor is further configured to cease applying the drift compensation function continuously to the data points when the measured change in sensitivity or baseline of the sensor is below a threshold value.

42. The system of claim 22, wherein the processor is further configured to cease applying the drift compensation function continuously to the data points after a predetermined amount of time has elapsed.

43. The system of claim 22, the processor configured to determine a drift compensation function based on the measured change in sensitivity or baseline of the sensor over the interval of time, and to apply the drift compensation function continuously to the data points over the next interval of time to continuously adjust the sensor data output to compensate for changes in sensitivity or baseline of the sensor over a second time interval.

* * * * *

UNITED STATES PATENT AND TRADEMARK OFFICE
CERTIFICATE OF CORRECTION

PATENT NO.        : 9,433,376 B2
APPLICATION NO.   : 13/796185
DATED             : September 6, 2016
INVENTOR(S)       : Estes et al.

It is certified that error appears in the above-identified patent and that said Letters Patent is hereby corrected as shown below:

In the Specification

In Column 9 at Line 6, After "boundary" insert --.--.

In Column 9 at Line 8 (approx.), After "boundary" insert --.--.

In Column 9 at Line 11 (approx.), After "boundary" insert --.--.

In Column 11 at Line 25, After "boundary" insert --.--.

In Column 11 at Line 27, After "boundary" insert --.--.

In Column 11 at Line 30, After "boundary" insert --.--.

In Column 18 at Line 49, After "user," insert --system calibrations using--.

In Column 18 at Line 51, After "may" delete "system calibrations using".

In Column 22 at Line 19, Change "that that" to --that--.

In Column 31 at Line 6, Change "the a" to --a--.

In Column 39 at Line 14, Change "($m_{implant}$)" to --($m_{implant}$),--.

Signed and Sealed this
Third Day of January, 2017

Michelle K. Lee
*Director of the United States Patent and Trademark Office*